US012560620B2

(12) United States Patent
Wilson et al.

(10) Patent No.: US 12,560,620 B2
(45) Date of Patent: Feb. 24, 2026

(54) PRO-ADM FOR PROGNOSIS OF TRAUMA-RELATED COMPLICATIONS IN POLYTRAUMA PATIENTS

(71) Applicant: B.R.A.H.M.S GMBH, Hennigsdorf (DE)

(72) Inventors: Darius Wilson, Lörrach (DE); Aline Pehla, Birkenwerder (DE); Stefan Ebmeyer, Hoppegarten (DE); Frauke Dreyer, Berlin (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 714 days.

(21) Appl. No.: 16/972,509

(22) PCT Filed: Jun. 6, 2019

(86) PCT No.: PCT/EP2019/064805
§ 371 (c)(1),
(2) Date: Dec. 4, 2020

(87) PCT Pub. No.: WO2019/234165
PCT Pub. Date: Dec. 12, 2019

(65) Prior Publication Data
US 2021/0405070 A1     Dec. 30, 2021

(30) Foreign Application Priority Data
Jun. 6, 2018     (EP) ..................................... 18176268

(51) Int. Cl.
*G01N 33/74* (2006.01)

(52) U.S. Cl.
CPC ....... *G01N 33/74* (2013.01); *G01N 2333/575* (2013.01)

(58) Field of Classification Search
None
See application file for complete search history.

(56) References Cited

U.S. PATENT DOCUMENTS

| | | | | |
|---|---|---|---|---|
| 11,041,867 | B2 * | 6/2021 | Wilson ............... | G01N 33/6893 |
| 2011/0086831 | A1 | 4/2011 | Bergmann et al. | |
| 2012/0094314 | A1 | 4/2012 | Bahrami et al. | |
| 2013/0203612 | A1 | 8/2013 | Graf et al. | |
| 2015/0011017 | A1 | 1/2015 | Bergmann et al. | |
| 2017/0010286 | A1 * | 1/2017 | Bergmann ............... | A61P 9/00 |

FOREIGN PATENT DOCUMENTS

| | | | |
|---|---|---|---|
| EP | 1488209 | A1 | 12/2004 |
| EP | 2320237 | A1 | 5/2011 |
| WO | 9707214 | A1 | 2/1997 |
| WO | 2002042770 | A1 | 5/2002 |
| WO | 2004090546 | A1 | 10/2004 |
| WO | 2008012019 | A2 | 1/2008 |
| WO | 2009062948 | A1 | 5/2009 |
| WO | 2010128071 | A1 | 11/2010 |
| WO | 2010139475 | A1 | 12/2010 |
| WO | 2011110565 | A1 | 9/2011 |
| WO | 2012059477 | A1 | 5/2012 |
| WO | 2013086359 | A1 | 6/2013 |
| WO | 2014147153 | A1 | 9/2014 |
| WO | WO-2017089474 | A1 * | 6/2017 .......... G01N 33/721 |
| WO | 2018007588 | A1 | 1/2018 |
| WO | 2018029214 | A1 | 2/2018 |
| WO | WO-2018029213 | A1 * | 2/2018 ............. G01N 33/68 |

OTHER PUBLICATIONS

Waiker et al (J Am Soc Nephrol. Jan. 2012; 23(1): 13-21) (Year: 2012).*
Mayeux (NeuroRx. Apr. 2004; 1(2):182-8) (Year: 2004).*
Mas-Celis et al (Archives of Medical Research, vol. 52, Issue 8, Nov. 2021, pp. 808-816) (Year: 2021).*
Dash et al (Neurotherapeutics. Jan. 2010;7(1):100-14) (Year: 2010).*
Ueda et al (Am J Respir Crit Care Med vol. 160. pp. 132-136, 1999) (Year: 1999).*
Grandic et al (Acta Clin Croat 2017; 56:453-459) (Year: 2017).*
Al Shuaibi, M., et al., "Pro-adrenomedullin as a Novel Biomarker for Predicting Infections and Response to Antimicrobials in Febrile Patients With Hematologic Malignancies," Clinical Infectious Diseases, vol. 56, No. 7, pp. 943-950 (Jan. 3, 2013).
Andaluz-Ojeda, D., et al., "Superior accuracy of mid-regional proadrenomedullin for mortality prediction in sepsis with varying levels of illness severity," Annals of Intensive Care, vol. 7, article No. 15, pp. 1-8 (Feb. 10, 2017).
Angeletti, S., et al., "Diagnostic and prognostic role of procalcitonin (PCT) and MR-pro-Adrenomedullin (MR-proADM) in bacterial infections," APMIS, vol. 123, No. 9, pp. 740-748 (Jun. 8, 2015).
Angeletti, S., et al., "Procalcitonin and mid-regional pro-adrenomedullin test combination in sepsis diagnosis," Clinical Chemistry and Laboratory Medicine, vol. 51, No. 5, pp. 1059-1067 (May 2013).
Bello, S., et al., "Prognostic power of proadrenomedullin in community-acquired pneumonia is independent of aetiology," European Respiratory Journal, vol. 39, pp. 1144-1155 (Nov. 10, 2011).
Caironi, P., et al., "Circulating Biologically Active Adrenomedullin such statement (bio-ADM) Predicts Hemodynamic support Requirement and Mortality During Sepsis," Chest, vol. 152, No. 2, pp. 312-320 (Apr. 11, 2017).

(Continued)

*Primary Examiner* — Brian Gangle
*Assistant Examiner* — Andrea K McCollum
(74) *Attorney, Agent, or Firm* — Millen, White, Zelano & Branigan P.C.; Ryan R. Pool

(57) ABSTRACT

The invention relates to a method for the diagnosis, prognosis, prediction, risk assessment and/or risk stratification of a subsequent trauma-related complication in a polytrauma patient, comprising providing a sample of said patient, wherein the sample is isolated from the patient after the polytrauma, determining a level of pro-adrenomedullin (proADM) or fragment(s) thereof in said sample, wherein said level of pro-adrenomedullin (proADM) or fragment(s) thereof correlates with the likelihood of a subsequent trauma-related complication.

20 Claims, No Drawings

Specification includes a Sequence Listing.

(56)                    References Cited

OTHER PUBLICATIONS

Cavallazzi, R., et al., "Midregional proadrenomedullin for prognosis in community-acquired pneumonia: a systematic review," Respiratory Medicine, vol. 108, pp. 1569-1580 (Oct. 6, 2014).

Charles, P.E., et al., "MR-ProADM elevation upon ICU admission predicts the outcome of septic patients and is correlated with upcoming fluid overload," Shock, vol. 48, No. 4, pp. 418-426 (Oct. 2017).

Christ-Crain, M., et al., "Biomarkers in respiratory tract infections: diagnostic guides to antibiotic prescription, prognostic markers and mediators," European Respiratory Journal, vol. 30, No. 3, pp. 556-573 (Aug. 31, 2007).

Christ-Crain, M., et al., "Mid-regional proadrenomedullin as a prognostic marker in sepsis: an study," Critical Care, vol. 9, No. 6, pp. R816-R824 (Nov. 15, 2005).

Christ-Crain, M., et al., "Procalcitonin Guidance of Antibiotic Therapy in Community-acquired Pneumonia: A Randomized Trial," American Journal of Respiratory Critical Care Medicine, vol. 174, pp. 84-93 (Apr. 7, 2006).

Courtais, C., et al., "Proadrenomedullin, a useful tool for risk stratification in high Pneumonia Severity Index score community acquired pneumonia," American Journal of Emergency Medicine, vol. 31, pp. 215-221 (Sep. 20, 2012).

Curbelo, J., et al., "Inflammation biomarkers in blood as mortality predictors in community-acquired pneumonia admitted patients: Importance of comparison with neutrophil count percentage or neutrophil-lymphocyte ratio," PLoS One, vol. 12, No. 3, pp. 1-14 (Mar. 16, 2017).

De Jong, E., et al., "Efficacy and safety of procalcitonin guidance in reducing the duration of antibiotic treatment in critically patients: a randomised, controlled, open-label trial," Lancet Infectious Diseases, vol. 16, pp. 819-827 (Feb. 29, 2016).

De La Torre-Prados, M.V., et al., "Mid-regional pro-adrenomedullin as prognostic biomarker in septic shock," Minerva Anestesiologica, vol. 82, No. 7, pp. 760-766 (Jul. 2016).

Debiane, L., et al., "The Utility of Proadrenomedullin and Procalcitonin in Comparison to C-reactive Protein as Predictors of Sepsis and Bloodstream Infections in Critically Ill Patients with Cancer," Critical Care Medicine, vol. 42, Issue 12, pp. 2500-2507 (Dec. 2014).

Decker, S., et al., "Immune-Response Patterns and Next Generation Sequencing Diagnostics for the Detection of Mycoses in Patients with Septic Shock-Results of a Combined Clinical and Experimental Investigation," International Journal of Molecular Sciences, vol. 18, No. 1796, pp. 1-32 (Aug. 18, 2017).

Elke, G., et al., "The use of mid-regional proadrenomedullin to identify disease severity and treatment response to sepsis—a secondary analysis of a large randomised controlled trial," Critical Care, vol. 22, No. 79, pp. 1-12 (Mar. 21, 2018).

Gille, J., et al., "MR-proADM: A New Biomarker for Early Diagnosis of Sepsis in Burned Patients," Journal of Burn Care & Research, vol. 38, pp. 290-298 (Sep./Oct. 2017).

Gordo-Remartinez, S., et al., "Usefulness of Midregional Proadrenomedullin to Predict Poor Outcome in Patients with Community Acquired Pneumonia," PLoS One, vol. 10, No. 6, pp. 1-15 (Jun. 1, 2015).

Guignant, C., et al., "Assessment of pro-vasopressin and pro-adrenomedullin as predictors of 28-day mortality in septic shock patients," Intensive Care Medicine, vol. 35, pp. 1859-1867 (Aug. 7, 2009).

Hartmann, O., et al., "Time-dependent Cox regression: Serial measurement of the cardiovascular biomarker proadrenomedullin improves survival prediction in patients with lower respiratory tract infection," International Journal of Cardiology, vol. 161, pp. 166-173 (Sep. 24, 2012).

Hoeboer, S., et al., "Old and new biomarkers for predicting high and low risk microbial infection in critically ill patients with new onset fever: a case for procalcitonin," Journal of Infection, vol. 64, pp. 484-493 (Jan. 8, 2012).

Huang, D., et al., "Midregional Proadrenomedullin as a Prognostic Tool in Community-Acquired Pneumonia," Chest, vol. 136, No. 3, pp. 823-831 (Sep. 2009).

International Search Report for PCT/EP2019/064805 issued on Aug. 2, 2019, 7 pages.

Kalayanarooj, S., "Clinical Manifestations and Management of Dengue/DHF/DSS," Tropical Medicine and Health, vol. 39, No. 4 Supplement, pp. 83-87 (Dec. 22, 2011).

Lundberg, O., et al., "Adrenomedullin and endothelin-1 are associated with myocardial injury and death in septic shock patients," Critical Care, vol. 20, No. 178, pp. 1-11 (Jun. 9, 2016).

Marino, R., et al., "Plasma adrenomedullin is associated with short-term mortality and vasopressor requirement in patients admitted with sepsis," Critical Care, vol. 18, No. R34, pp. 1-7 (Feb. 17, 2014).

Michels, M., et al., "High plasma mid-regional pro-adrenomedullin levels in children with severe dengue virus infections," Journal of Clinical Virology, vol. 50, issue 1, pp. 8-12 (Oct. 16, 2010).

Pereira, J.M., et al., "Mid-regional proadrenomedullin: An early marker of response in critically community-acquired pneumonia?," Revista Portuguesa de Pneumologia (English Edition), vol. 22, No. 6, pp. 308-314 (May 6, 2016).

Renaud, B., et al., "Proadrenomedullin improves Risk of Early Admission to ICU score for predicting early severe community-acquired pneumonia," Chest, vol. 142, No. 6, pp. 1447-1454 (Dec. 2012).

Saeed, K., et al., "The early identification of disease progression in patients with suspected infection presenting to the emergency department: a multi-centre derivation and validation study," Critical Care, vol. 23, No. 40, pp. 1-15 (Feb. 8, 2019).

Schuetz, P., et al., "Blood biomarkers for personalized treatment and patient management decisions in community-acquired pneumonia," Current Opinion in Infectious Diseases, vol. 26, pp. 159-167 (Apr. 2013).

Schuetz, P., et al., "Circulating Precursor Levels of Endothelin-1 and Adrenomedullin, Two Endothelium-Derived, Counteracting Substances, in Sepsis," Endothelium, vol. 14, pp. 345-351 (Jul. 13, 2009).

Suberviola, B., et al., "Hospital mortality prognostication in sepsis using the new biomarkers suPAR and proADM in a single determination on ICU admission," Intensive Care Medicine, pp. 1-11 (Aug. 16, 2013).

Suberviola, B., et al., "Prognostic value of proadrenomedullin in severe sepsis and septic shock patients with community-acquired pneumonia," Swiss Medical Weekly, vol. 142, No. w13542, pp. 1-8 (Mar. 19, 2012).

Thanachartwet, V., et al., "Serum Procalcitonin and Peripheral Venous Lactate for Predicting Dengue Shock and/or Organ Failure: A Prospective Observational Study," PLoS Neglected Tropical Diseases, vol. 10, No. 8, pp. 1-19 (Aug. 26, 2016).

Travaglino, F., et al., "Utility of Procalcitonin (PCT) and Mid regional pro-Adrenomedullin (MR-proADM) in risk stratification of critically ill febrile patients in Emergency Department (Ed). A comparison with APACHE II score," BMC Infectious Diseases, vol. 12, No. 184, pp. 1-8 (Aug. 8, 2012).

Ueda, S., et al., "Increased plasma levels of adrenomedullin in patients with systemic inflammatory response syndrome," American Journal of Respiratory and Critical Care Medicine, vol. 160, No. 1, pp. 132-136 (Jul. 1999).

Viaggi, B., et al., "Mid regional pro-adrenomedullin for the prediction of organ failure in infection. Results from a single centre study," PLoS One, vol. 13, No. 8, pp. 1-10 (Aug. 13, 2018).

Wang, R. L., et al., "Prediction about severity and outcome of sepsis by pro-atrial natriuretic peptide and pro-adrenomedullin," Chinese Journal of Traumatology, vol. 13, No. 3, pp. 152-157 (Jun. 10, 2010).

Gluhovschi, G., et al., "Multi-organ protection and the kidney. From nephroprotection, cardioprotection, neuroprotection to multi-organ protection," Nefrologia, vol. 24, No. 6, pp. 519-535 (Sep. 27, 2004).

* cited by examiner

PRO-ADM FOR PROGNOSIS OF TRAUMA-RELATED COMPLICATIONS IN POLYTRAUMA PATIENTS

CROSS-REFERENCE TO RELATED APPLICATIONS

This application is a national phase entry pursuant to 35 U.S.C. § 371 of International Application No. PCT/EP2019/064805, filed on Jun. 6, 2019, which claims the benefit of priority to European Patent Application serial number 18176268.3 filed on Jun. 6, 2018, both of which are incorporated by reference in their entirety.

The invention relates to a method for the diagnosis, prognosis, prediction, risk assessment and/or risk stratification of a subsequent trauma-related complication in a polytrauma patient, comprising providing a sample of said patient, wherein the sample is isolated from the patient after the polytrauma, determining a level of proADM or fragment(s) thereof in said sample, wherein said level of proADM or fragment(s) thereof correlates with the likelihood of a subsequent trauma-related complication.

BACKGROUND OF THE INVENTION

The treatment of severely injured patients following multiple trauma represents an increasing and significant burden on healthcare providers [1-3], with the subsequent development of systemic inflammation making an early identification of sepsis problematic [4, 5]. Despite decreasing mortality rates due to the initial trauma, the incidence of sepsis as a subsequent complication remains unaltered and can result in prolonged periods of intensive care treatment and higher mortality rates [3]. Thus, an early and accurate identification of a patient's potential for subsequent sepsis development may be of significant clinical value. Conversely, the rule out of sepsis development is of equal importance in terms of withholding antibiotics, or conducting additional sepsis-related investigations, such as focus cleaning.

Furthermore, polytrauma patients tend to develop further trauma-related complications that are not necessarily related to an infection, including rhabdomyolysis and organ failure, which can lead to prolonged periods of intensive care treatment and higher mortality rates. For such non-infection related complications a method for early identification of polytrauma patients at risk of developing such complications is also urgently needed.

The use of biomarkers to distinguish between the presence of significant systemic inflammation and the early stages of sepsis development or non-infection related complications may allow for the initiation of personalized treatment strategies, such as an earlier initiation of antibiotic therapy. Biomarkers such as C-reactive protein (CRP), procalcitonin (PCT) and interleukin (IL)-6 have been incorporated into routine clinical use [6, 7], with other biomarkers and clinical scores, such as lactate, the sequential organ failure assessment (SOFA) score, and recently proposed quick SOFA score, form key parts of the recently revised sepsis definitions [8]. Despite the presence of these established biomarkers and scores, there still remains a clinical requirement for earlier and more accurate tools to aid in the prediction and identification of developing infection and non-infection related complications in severely injured patients, and in particular polytrauma patients.

Accordingly, a need exists in the field of treating severely injured patients, such as polytrauma patients, for additional means for diagnosis, prognosis, prediction, risk assessment and/or risk stratification of a subsequent trauma-related complication.

Employing proADM represents such means, in particular mid-regional proadrenomedullin (MR-proADM). Recent studies have shown concentrations to be increased earlier in patients who develop sepsis following burns [9] and neurological injury [10], with extensive evidence previously published concerning its use in identifying disease severity in already infected patients [11-13].

Wang et al (Chinese Journal Of Traumatology (English Edition), vol. 13, no. 3, 1 Jun. 2010, pages 152-157) have shown that proADM can be used as a marker for the severity of sepsis and mortality of ICU patients. However, Wang et al are silent about the use of proADM for predicting sepsis in the specific subgroup of polytrauma patients, and accordingly also no specific cut-off values for this patient collective have been investigated. Furthermore, WO2018/029214A1 describes a method for predicting complications in a subject, wherein the subject can be for example a healthy subject or a subject suffering from a respiratory disease, urinary tract infection or malignancy.

Accordingly, no previous investigation has addressed the performance of proADM in patients following severe trauma, such as in patients with an Injury Severity Score (ISS) of ≥17 points or in polytrauma patients. However, the selection of a specific subgroup of patients can have an enormous influence on the performance of biomarkers, such as proADM, such that the predictive impact of a certain level of a biomarker depends on the patient reference group.

US patent applications US2013/203612A1 and US2012/094314A1 refer to methods for predicting sepsis in polytrauma patients, but with markers other than proADM. US2013/203612A1 relates to the use of pancreatic stone protein and US2012/094314A1 describes the use of NT-CNP. Both of these biomarkers are completely unrelated to proADM and there is no indication that proADM could be used as an alternative to these markers in a method similar to the methods described in these disclosures.

The data disclosed herein compares the performance of MR-proADM with already established biomarkers (PCT, CRP and lactate) and clinical severity scores (SOFA) in order to: (i) compare concentrations immediately after trauma, (ii) assess performance in identifying patients at risk of developing an infection related complication, (iii) identifying patients with a lower risk of any subsequent sepsis development, and (iv) identifying patients at risk of developing a non-infection related complication.

SUMMARY OF THE INVENTION

In light of the difficulties in the prior art, the technical problem underlying the present invention is the provision of means for diagnosis, prognosis, prediction, risk assessment and/or risk stratification of a subsequent trauma-related complication in a polytrauma patient.

The present invention therefore seeks to provide methods, kits and further means for diagnosis, prognosis, prediction, risk assessment and/or risk stratification of a subsequent trauma-related complication in a polytrauma patient on the basis of adrenomedullin (ADM) levels, in particular proADM or MR-proADM, determined in a sample from a patient. One object of the invention is therefore the use of a biomarker or combination of biomarkers to distinguish polytrauma patients who are more likely or have a high risk of a subsequent trauma-related complication, such as sepsis or rhabdomyolysis, polytrauma patients who have a low risk of a subsequent trauma-related complication.

The solution to the technical problem of the invention is provided in the independent claims. Preferred embodiments of the invention are provided in the dependent claims.

The invention therefore relates to a method for the diagnosis, prognosis, prediction, risk assessment and/or risk stratification of a subsequent trauma-related complication in a polytrauma patient, comprising providing a sample of said patient, wherein the sample is isolated from the patient after the polytrauma, determining a level of proADM or fragment(s) thereof in said sample, wherein said level of proADM or fragment(s) thereof correlates with the likelihood of a subsequent trauma-related complication.

The present invention provides a new, quick and reliable test for healthcare practitioners, such as doctors, nurses, personnel in emergency departments etc., to quickly assess the risk of a polytrauma patient to develop of trauma-related complication, such as for sepsis. Due to the unspecific increase of many inflammatory markers and other signs of inflammation after polytrauma, it is difficult for medical personnel to differentiate between inflammation and the development of a trauma-related complication, which may also be associated with signs of inflammation, such as an infection, sepsis, organ failure, shock, and rhabdomyolysis. Surprisingly, the present invention provides means for identifying patients that have an increased or high risk of developing trauma-related complications and also identify patients that are less likely to develop such complications or in which the development of such complications can be practically ruled out, by determining the level of proADM or fragments thereof in a sample isolated from the patient.

In embodiments of the invention, the patient may be a severely injured patient instead of a polytrauma patient. In embodiments of the invention, the severely injured patient may be a polytrauma patient. In embodiments of the invention, polytrauma patients may be considered to be severely injured. According to the present invention, a trauma-related complication can be considered as an adverse event in the health of the patient.

It is a great advantage that this is possible by isolating a sample early on after the occurrence of the polytrauma, providing medical personnel with early guidance on the progression of the state of the patient and thereby enabling directed and improved therapeutic decision making, for example with respect to the administration of specific medicaments of treatment measures. It is a further advantage that the level of proADM can also be determined at later time points after polytrauma and therefore enables monitoring of the health status of the patient.

In embodiments of the invention, the sample is isolated from said patient within 48 hours, preferably within 24 hours, more preferably within 6 hours after the polytrauma.

In embodiments, the sample is isolated from said patient within about 30 minutes, 1 hour, 2 hours, 3 hours, 4, hours, 5 hours, 6 hours, 7 hours, 8 hours, 9 hours, 10 hours, 11 hours, 12 hours, 14 hours, 16 hours, 18 hours, 20 hours 22 hours, 24 hours, 30 hours, 36 hours, 42 hours, 48 hours, 60 hours, 72 hours, 84 hours, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days or 28 days after the polytrauma.

In embodiments of the invention, more than one sample may be isolated from the patient for determining proADM or fragment(s) thereof at multiple time points after polytrauma.

In further embodiments of the invention, the patient, who may be a severely injured and/or a polytrauma patient, has an Injury Severity Score (ISS) of points. In preferred embodiments, the polytrauma patient has an ISS ≥17 of points. It has been shown that the method of the invention is particularly accurate in severely injured patients with an ISS of ≥17, which is very useful since such patients are particularly instable and trauma-related complications may be detrimental for the health status of these patients. Accordingly, the method of the invention enables an improved management of the patient, focusing on the real needs, while it may be possible to rule out potentially occurring complications. By ruling out potentially occurring complications, a certain therapy can be adjusted or discontinued to avoid the development of severe side effects that polytrauma patients could face.

Furthermore, in some embodiments, the group of severely injured and/or polytrauma patients concerned by the method of the invention does not include patients with an ISS of less than 15, less than 16, less than 17, less than 18, less than 19 or less than 20. Furthermore, in some embodiments, the patients of the invention may not comprise burn patients with a burned total body surface area (TBSA) below 40%, 39%, 38%, 37%, 36% or 35%. Furthermore, trauma patients with an ISS of 9, 10, 11, 12, 13 or 14 may in some embodiments be excluded from the method of the invention. In embodiments of the invention, the method relates to patients with an ISS of 15 or more, 16 or more, 17 or more, 18 or more, 19 or more or 20 or more.

The severity of a trauma, such as a burn, can have an influence on the level of proADM and its predictive value for trauma related complications so that the selection of the correct group of polytrauma patients can be decisive for successfully performing the method of the present invention. Accordingly, performing the method on a patient that has a trauma but does not qualify as polytrauma patient in the sense of the invention may lead to false or misleading results. However, a polytrauma patient in the sense of the invention does not necessarily have to suffer from multiple injuries, such as two or more injuries in at least two areas of the body or a condition with a multiple injury, i.e. two or more severe injuries in one body area. It is also possible that a polytrauma patient only suffers from one severe injury that qualifies as a polytrauma, such as a burn of more than 40% of the TBSA.

In preferred embodiment of the present invention, a level of proADM or fragment(s) thereof equal or above 1.54 nmol/l±20%, preferably equal or above 1.54 nmol/l±10%, more preferably equal or above 1.54 nmol/l is indicative of a subsequent trauma-related complication.

In further embodiments, a level of proADM or fragment(s) thereof below 1.54 nmol/l±20%, preferably below 1.54 nmol/l±10%, more preferably below 1.54 nmol/l is indicative of the absence of a subsequent trauma-related complication.

It is a great advantage of the method of the invention that by using a cut-off values of 1.54 nmol/l±20% it is possible to identify patients with a higher risk of developing trauma-related complications and/or also identify patients, which are unlikely to develop such complications or in which such complications can be practically ruled out, irrespective of a specific time point or time a restricted time window of sample isolation after occurrence of the polytrauma and irrespective of the specific trauma related complication.

According to the present invention, the term "indicate" in the context of "indicative of a subsequent adverse event", "indicative of a subsequent trauma-related complication", "indicative of the absence of a subsequent adverse event" and "indicative of the absence of a subsequent trauma-related complication" is intended as a measure of risk and/or likelihood. Preferably, the "indication" of the presence or absence of an adverse event is intended as a risk assessment, and is typically not to be construed in a limiting fashion as to point definitively to the absolute presence or absence of said event.

Therefore, the terms "indicative of a subsequent adverse event", "indicative of a subsequent trauma-related complication", "indicative of the absence of a subsequent adverse event" and "indicative of the absence of a subsequent trauma-related complication" can be understood as indicating a low or high risk of the occurrence of an adverse event/trauma-related complication, respectively. In some embodiments a low risk relates to a lower risk compared to proADM levels detected above the indicated values. In some embodiments a high risk relates to a higher risk compared to proADM levels detected below the indicated values.

Keeping the above in mind, the determination of high and low severity levels of proADM is however very reliable with respect to determining the presence or absence of a subsequent adverse event when using the cut-off values disclosed herein, such that the estimation of risk enables an appropriate action by a medical professional.

It was entirely surprising that a level of proADM or fragments thereof could be correlated with the likelihood of the presence or absence of a subsequent trauma-related complication in the context of polytrauma patients. proADM levels in samples from polytrauma patients of the present invention can preferably be assigned to at least two different severity levels of proADM (high and low). High levels of proADM indicate a high severity level and low levels indicate a low severity levels. The respective concentrations that determine the cut-off value, which may be used to assign the respective severity levels, may depend on multiple parameters such as the time point of sample isolation after polytrauma, the trauma-related complication to be assessed by the method and the method used for determining the level of proADM or fragments thereof in said sample.

The cut-off values disclosed herein refer preferably to measurements of the protein level of proADM or fragments thereof in a blood sample, preferably a whole blood sample or plasma or serum sample obtained from a patient, by means of the Thermo Scientific B•R•A•H•M•S KRYPTOR® assay. Accordingly, the values disclosed herein may vary to some extent depending on the detection/measurement method employed, and the specific values disclosed herein are intended to also read on the corresponding values determined by other methods.

In embodiments of the invention, the limiting value or cut-off value of proADM or fragment(s) thereof that may define the transition from a low to a high severity level may be any value in the range of 0.1 nmol/l and 4 nmol/l. Any value within this range may be considered an appropriate cut-off value for high and low proADM severity levels. Furthermore, values below such a cut-off value may be indicative of the absence of a trauma-related complication, and values equal or above such a cut-off value may be indicative of a trauma-related complication. Appropriate cut-off levels that may be used in the context of the present invention, comprise, without limitation, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0 nmol/l.

In embodiments of the invention, deviations from these possible cut-off values are also claimed, such as deviations of ±30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1%.

In certain embodiments of the method of the invention, the trauma-related complication comprise infection-related complication, such as an infection, a nosocomial infection, sepsis and/or septic shock. In certain embodiments of the method of the invention, the trauma-related complication comprise an infection, a nosocomial infection, sepsis and/or septic shock. In further embodiments, the trauma-related complications consist of infection-related complications, such as an infection, a nosocomial infection, sepsis and/or septic shock. In embodiments, the trauma-related complication is sepsis.

In embodiments of the invention, a level of proADM or fragment(s) thereof in a sample isolated within 24 hours after the severe injury equal or above 0.97 nmol/l±20%, preferably equal or above 0.97±10%, more preferably equal or above 0.97 nmol/l is indicative of a subsequent infection, nosocomial infection, sepsis and/or septic shock, and/or a level of proADM or fragment(s) thereof in a sample isolated between 24 and 48 hours after the severe injury equal or above 1.35 nmol/l±20%, preferably equal or above 1.35 nmol/l±10%, more preferably equal or above 1.35 nmol/l is indicative of a subsequent infection, nosocomial infection, sepsis and/or septic shock.

In embodiments of the invention, a level of proADM or fragment(s) thereof in a sample isolated within 24 hours after the severe injury below 0.97 nmol/l±20%, preferably below 0.97±10%, more preferably below 0.97 nmol/l is indicative of the absence of a subsequent infection, nosocomial infection, sepsis and/or septic shock, and/or a level of proADM or fragment(s) thereof in a sample isolated between 24 and 48 hours after the severe injury below 1.35 nmol/l±20%, preferably below 1.35 nmol/l±10%, more preferably below 1.35 nmol/l is indicative of the absence of a subsequent infection, nosocomial infection, sepsis and/or septic shock.

In embodiments of the invention, a level of proADM or fragment(s) thereof in a sample isolated within 24 hours after the severe injury equal or above 0.8 nmol/l, preferably equal or above 0.9 nmol/l, more preferably equal or above 0.97 nmol/l is indicative of a subsequent infection, nosocomial infection, sepsis and/or septic shock, and/or a level of proADM or fragment(s) thereof in a sample isolated between 24 and 48 hours after the severe injury equal or above 1.2 nmol/l, preferably equal or above 1.3 nmol/l, more preferably equal or above 1.35 nmol/l is indicative of a subsequent infection, nosocomial infection, sepsis and/or septic shock.

In embodiments of the invention, a level of proADM or fragment(s) thereof in a sample isolated within 24 hours after the severe injury below 0.8 nmol/l, preferably below 0.9 nmol/l, more preferably below 0.97 nmol/l is indicative of the absence of a subsequent infection, nosocomial infection, sepsis and/or septic shock, and/or a level of proADM or fragment(s) thereof in a sample isolated between 24 and 48 hours after the severe injury below 1.2 nmol/l, preferably below 1.3 nmol/l, more preferably below 1.35 nmol/l is indicative of the absence of a subsequent infection, nosocomial infection, sepsis and/or septic shock.

It is particular advantage that the cut-off of proADM or fragment(s) thereof to be used in the context of the method of the invention can be adjusted to the time-point of sample isolation and to the trauma-related complication to be detected or ruled-out. Accordingly, the method enables a more accurate assessment of the prognosis/risk of a patient depending on the situation of sample isolation and the further information available at that time, for example an increased risk of developing a specific trauma-related complication.

In further embodiments of the invention, the trauma-related complication comprises a non-infection related complications, such as rhabdomyolysis and/or organ failure. In embodiments, the trauma-related complication is rhabdomyolysis.

In embodiments of the invention, a level of proADM or fragment(s) thereof in a sample isolated within 24 hours after the severe injury equal or above 0.82 nmol/l±20%, preferably equal or above 0.82 nmol/l±10%, more preferably equal or above 0.82 nmol/l is indicative of a subsequent non-infection related complication, such as rhabdomyolysis and/or organ failure, and/or a level of proADM or fragment(s) thereof in a sample isolated between 24 and 48 hours after the severe injury equal or above 0.97 nmol/l±20%, preferably equal or above 0.97 nmol/l±10%, more preferably equal or above 0.97 nmol/l is indicative of a subsequent non-infection related complication, such as rhabdomyolysis and/or organ failure.

In embodiments of the invention, a level of proADM or fragment(s) thereof in a sample isolated within 24 hours after the severe injury below 0.82 nmol/l±20%, preferably below 0.82 nmol/l±10%, more preferably below 0.82 nmol/l is indicative of the absence of a subsequent non-infection related complication, such as rhabdomyolysis and/or organ failure, and/or a level of proADM or fragment(s) thereof in a sample isolated between 24 and 48 hours after the severe injury below 0.97 nmol/l±20%, preferably below 0.97 nmol/l±10%, more preferably below 0.97 nmol/l is indicative of the absence of a subsequent non-infection related complication, such as rhabdomyolysis and/or organ failure.

In embodiments of the invention, a level of proADM or fragment(s) thereof in a sample isolated within 24 hours after the severe injury equal or above 0.7 nmol/l, preferably equal or above 0.8 nmol/l, more preferably equal or above 0.82 nmol/l is indicative of a subsequent non-infection related complication, such as rhabdomyolysis and/or organ failure, and/or a level of proADM or fragment(s) thereof in a sample isolated between 24 and 48 hours after the severe injury equal or above 0.8 nmol/l, preferably equal or above 0.9 nmol/l, more preferably equal or above 0.97 nmol/l is indicative of a subsequent non-infection related complication, such as rhabdomyolysis and/or organ failure.

In embodiments of the invention, a level of proADM or fragment(s) thereof in a sample isolated within 24 hours after the severe injury below 0.7 nmol/l, preferably below 0.8 nmol/l, more preferably below 0.82 nmol/l is indicative of the absence of a subsequent non-infection related complication, such as rhabdomyolysis and/or organ failure, and/or a level of proADM or fragment(s) thereof in a sample isolated between 24 and 48 hours after the severe injury below 0.8 nmol/l, preferably below 0.9 nmol/l, more preferably below 0.97 nmol/l is indicative of the absence of a subsequent non-infection related complication, such as rhabdomyolysis and/or organ failure.

According to further embodiments of the method of the invention, the trauma-related complication comprises death. In embodiments, the trauma-related complication is death, preferably death within 28 days from the polytrauma. Preferably, in the context of the method of the invention the trauma-related complication (to be predicted) would occur within 28 days from the polytrauma.

In further embodiments, the trauma-related complication (to be predicted) would occur within 28, 27, 26, 25, 24, 23, 22, 21, 20, 19, 18, 17, 16, 15, 14, 13, 12, 11, 10, 9, 8, 7, 6, 5, 4, 3 or 2 days or 1 day from the polytrauma.

It is a great advantage of the present invention that it is possible to not only estimate the risk of a post-traumatic complication, but also provide a time frame for the occurrence of such complications so that the urgency of taking counteracting measures and the suitability of certain measures can be estimated.

Depending on the result of the method of the present invention, embodiments of the method may comprise subsequent therapeutic decisions and/or therapeutic actions. Such therapeutic decisions may include the initiation, change or modification of medical treatment. For example, if the method of the present invention is indicative of a subsequent trauma-related complication, suitable therapeutic measures, such as initiation or change of a certain medication, surgery or fluid therapy may be initiated. Any therapy, medical treatment or therapeutic action disclosed herein can be employed in the context of the method of the invention as a subsequent therapeutic decision or therapeutic action, in particular if the therapeutic measure is specific to the complication, such as for example antibiotic treatment in the case of sepsis, or in the case of rhabdomyolysis as a trauma-related complication, intravenous fluid therapy, dialysis, management of electrolyte abnormalities (in particular potassium, calcium and phosphorus). Furthermore, a maintained intensive observation and care of the patient may be indicated potentially over extended periods of time, such as several day, weeks or even months. This may involve keeping or moving the patient to an ICU and/or prolonging the stay of the patient in an ICU.

On the other hand, if the result of the method of the present invention is indicative of the absence of a trauma-related complication, no specific treatment measures with respect to such complication may be required.

On the contrary, if the method of the present invention is indicative of the absence of a subsequent trauma-related complication, this may indicate discontinuation or change of an unnecessary medication, such as for (intravenous) antibiotic therapy, and/or earlier discharge of the patient from an intensive care unit.

If the method of the present invention is indicative an infection, a nosocomial infection, sepsis and/or septic shock an antibiotic therapy may be initiated or an ongoing antibiotic therapy may be modified or changed.

In one embodiment the invention additionally comprises informing the patient of the results of the diagnostic method described herein. In embodiments of the invention, the patient is at least 18 years old.

In embodiments of the invention, the sample is selected from the group consisting of a blood sample, a serum sample, a plasma sample and/or a urine sample. Determining proADM or fragment(s) thereof in blood, serum or plasma is particularly advantageous since it has been shown to be particularly accurate. Furthermore, these samples reflect the actual status of the patient at a given time-point very accurately.

In embodiments of the invention, determining a level of proADM or fragment(s) thereof comprises determining a level of MR-proADM in the sample. The employment of determining MR-proADM is preferred for any given embodiment described herein and may be considered in the context of each embodiment, accordingly. In preferred embodiments the "ADM fragment" may be considered to be MR-proADM.

In further embodiments of the invention the level of proADM or fragment(s) thereof correlates with the likelihood of a subsequent trauma-related complication of said patient. In a preferred embodiment the level of proADM or fragment(s) thereof positively correlates with the likelihood of a subsequent trauma-related complication of said patient. In other words, the higher the level of proADM determined, the greater the likelihood of a subsequent trauma-related complication.

According to certain embodiments, the method of the invention additionally comprises determining a level of at least one additional biomarker or fragment(s) thereof in a sample from said patient, wherein the at least one additional biomarker preferably is PCT or fragment(s) thereof and/or lactate, and/or determining at least one clinical score, wherein the at least one clinical score is preferably SOFA, wherein the level of the at least one additional biomarker and/or the at least one clinical score, and the level of proADM or fragment(s) thereof is indicative of a subsequent trauma-related complication.

Further additional markers that may be determined in the context of the present invention comprise lactate and CRP. Clinical scores that may be determined in the context of the present invention comprise SI score (systemic inflammation score), SOFA, qSOFA, SIRS, SAPS II, APACHE II, preferably SOFA.

Determining proADM or fragment(s) thereof and SOFA in the context of the method of the invention turned out to provide further accuracy with respect to prediction and/or prognosis of a subsequent trauma-related complication, in particular if the trauma-related complication is or comprises sepsis.

In another embodiment of the method of the invention, the additional marker is lactate. Surprisingly, the combined determination of proADM and lactate in the context of the method of the invention provides a particularly accurate predication of a subsequent non-infection related complications, in particular rhabdomyolysis.

In further embodiments, the at least one additional biomarker is at least one marker of rhabdomyolysis, such as creatine kinase (CK), lactate dehydrogenase (LDH), creatinine, myoglobin, aldolase, troponin, carbonic anhydrase type 3, fatty acid-binding protein (FABP), transaminases or potassium.

In embodiments of the invention, the method additionally comprises determining a severity level of proADM or fragment(s) thereof in a first sample isolated from the polytrauma patient, and/or determining a severity level of proADM or fragment(s) thereof in a second sample isolated from said patient, wherein said second sample has been isolated after the first sample, wherein a level of proADM or fragment(s) thereof below 1.54 nmol/l±20% corresponds to a low severity level and a level of proADM or fragment(s) thereof equal or above 1.54 nmol/l±20% corresponds to a high severity level.

Preferably, the first sample is isolated from the polytrauma patient within 24 hours or more preferably within 6 hours after the polytrauma. The first sample may be isolated at any time-point disclosed for sample isolation in the context of the method of the invention.

Furthermore, the second sample may be isolated from said patient within 24 hours after the isolation of the first sample. However, the second sample may be isolation within about 30 minutes, 1 hour, 2 hours, 3 hours, 4, hours, 5 hours, 6 hours, 7 hours, 8 hours, 9 hours, 10 hours, 11 hours, 12 hours, 14 hours, 16 hours, 18 hours, 20 hours 22 hours, 24 hours, 30 hours, 36 hours, 42 hours, 48 hours, 60 hours, 72 hours, 84 hours, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days or 28 days after isolation of the first sample.

In embodiments of the invention, a high severity level of proADM or fragment(s) thereof in the second sample is indicative of a subsequent trauma related complication. In further embodiments of the invention, an increasing severity level of proADM or fragment(s) thereof in the second sample as compare to the first sample is indicative of a subsequent trauma related complication.

In further embodiments, a low severity level of proADM or fragment(s) thereof in the first and the second sample is indicative of the absence of a subsequent trauma related complication, such as preferably sepsis and/or septic shock. Furthermore, a low severity level of proADM or fragment (s) thereof in the second sample may be indicative of the absence of a subsequent trauma related complication, such as preferably sepsis and/or septic shock.

In embodiments of the invention, continuously low severity levels of proADM or fragment(s) thereof are indicative of the absence of infection-related complication, in particular sepsis, and preferably the occurrence of sepsis (preferably within 28 days from polytrauma) can be ruled out in case of continuously low proADM severity levels.

Furthermore, the present invention relates to a kit for carrying out the method of the invention, comprising detection reagents for determining the level proADM or fragment(s) thereof, and optionally additionally for determining the level of at least one additional biomarker such as PCT or fragment(s) thereof and/or lactate, in a sample from a subject, and reference data, such as reference level, corresponding to
      i. a level of proADM or fragment(s) thereof in a sample isolated within 24 hours after the severe injury equal or above 0.97 nmol/l±20% for the diagnosis, prognosis, prediction, risk assessment and/or risk stratification of a subsequent infection, nosocomial infection, sepsis and/or septic shock, ii. a level of proADM or fragment(s) thereof in a sample isolated between 24 and 48 hours after the severe injury equal or above 1.35 nmol/l±20% for the diagnosis, prognosis, prediction, risk assessment and/or risk stratification of a subsequent infection, nosocomial infection, sepsis and/or septic shock, iii. a level of proADM or fragment(s) thereof in a sample isolated within 24 hours after the severe injury equal or above 0.82 nmol/l±20% for the diagnosis, prognosis, prediction, risk assessment and/or risk stratification of a subsequent non-infection related complication, such as rhabdomyolysis and/or organ failure, iv. a level of proADM or fragment(s) thereof in a sample isolated between 24 and 48 hours after the severe injury equal or above 0.97 nmol/l±20% for the diagnosis, prognosis, prediction, risk assessment and/or risk stratification of a subsequent non-infection related complication, such as rhabdomyolysis and/or organ failure, and/or v. high and/or low severity levels of proADM or fragment(s) thereof, wherein the low severity level is below 1.54 nmol/l±20% and the high severity level is equal or above 1.54 nmol/l±20%, wherein said reference data is preferably stored on a computer readable medium and/or employed in in the form of computer executable code configured for comparing the determined levels of proADM or fragment(s) thereof, and optionally additionally the determined levels of at least one additional biomarker such as PCT or fragment(s) thereof and/or lactate, to said reference data.

The detection reagents for determining the level of proADM or fragment(s) thereof, and optionally for determining the level of PCT, lactate and/or C-reactive protein or fragment(s) thereof, are preferably selected from those necessary to perform the method, for example antibodies directed to ADM, suitable labels, such as fluorescent labels, preferably two separate fluorescent labels suitable for application in the KRYPTOR® assay, sample collection tubes.

The embodiments and features disclosed in the context of the method of the invention also apply to the kit of the present invention and the other way around.

In one embodiment of the method described herein the level of proADM or fragment(s) thereof and optionally additionally other biomarkers such as for example PCT or fragment(s) thereof is determined using a method selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analyzers.

The method according to the present invention can furthermore be embodied as a homogeneous method, wherein the sandwich complexes formed by the antibody/antibodies and the marker, e.g., the proADM or a fragment thereof, which is to be detected remains suspended in the liquid phase. In this case it is preferred, that when two antibodies are used, both antibodies are labelled with parts of a detection system, which leads to generation of a signal or triggering of a signal if both antibodies are integrated into a single sandwich.

Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733 A, EP-B1 0 180 492 or EP-B1 0 539 477 and the prior art cited therein. In this way, measurements in which only reaction products comprising both labelling components in a single immune-complex directly in the reaction mixture are detected, become possible.

For example, such technologies are offered under the brand names TRACE® (Time Resolved Amplified Cryptate Emission) technology or KRYPTOR® assay, implementing the teachings of the above-cited applications. Therefore, in particular preferred aspects, a diagnostic device is used to carry out the herein provided method. For example, the level of the proADM protein or a fragment thereof, and/or the level of any further marker of the herein provided method are determined. In particular preferred aspects, the diagnostic device is KRYPTOR® assay.

In one embodiment of the method described herein the method is an immunoassay and wherein the assay is performed in homogeneous phase or in heterogeneous phase.

In further embodiments of the method described herein, the method additionally comprises a molecular analysis of a sample from said patient for detecting an infection. The sample used for the molecular analysis for detecting an infection preferably is a blood sample. In a preferred embodiment the molecular analysis is a method aiming to detect one or more biomolecules derived from a pathogen. Said one or more biomolecule may be a nucleic acid, protein, sugar, carbohydrades, lipid and or a combination thereof such as glycosylated protein, preferably a nucleic acid. Said biomolecule preferably is specific for one or more pathogen(s). According to preferred embodiments, such biomolecules are detected by one or more methods for analysis of biomolecules selected from the group comprising nucleic acid amplification methods such as PCR, qPCR, RT-PCR, qRT-PCR or isothermal amplification, mass spectrometry, detection of enzymatic activity and immunoassay based detection methods. Further methods of molecular analysis are known to the person skilled in the art and are comprised by the method of the present invention.

In one embodiment of the method described herein a first antibody and a second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to said proADM or fragments thereof to be detected, a measurable signal which permits detection of the resulting sandwich complexes in the measuring solution is generated.

In one embodiment of the method described herein the labelling system comprises a rare earth cryptate or chelate in combination with a fluorescent or chemiluminescent dye, in particular of the cyanine type.

In one embodiment of the method described herein, the method additionally comprises comparing the determined level of proADM or fragment(s) thereof to a reference level, threshold value and/or a population average corresponding to proADM or fragments thereof in patients who have been diagnosed as being critically ill and are under medical treatment, wherein said comparing is carried out in a computer processor using computer executable code.

The methods of the present invention may in part be computer-implemented. For example, the step of comparing the detected level of a marker, e.g. the proADM or fragments thereof, with a reference level can be performed in a computer system. In the computer-system, the determined level of the marker(s) can be combined with other marker levels and/or parameters of the subject in order to calculate a score, which is indicative for the diagnosis, prognosis, prediction, risk assessment and/or risk stratification. For example, the determined values may be entered (either manually by a health professional or automatically from the device(s) in which the respective marker level(s) has/have been determined) into the computer-system. The computer-system can be directly at the point-of-care (e.g. primary care, ICU or ED) or it can be at a remote location connected via a computer network (e.g. via the internet, or specialized medical cloud-systems, optionally combinable with other IT-systems or platforms such as hospital information systems (HIS)). Typically, the computer-system will store the values (e.g. marker level or parameters such as age, blood pressure, weight, sex, etc. or clinical scoring systems such as SOFA, qSOFA, BMI etc.) on a computer-readable medium and calculate the score based-on pre-defined and/or pre-stored reference levels or reference values. The resulting score will be displayed and/or printed for the user (typically a health professional such as a physician). Alternatively or in addition, the associated prognosis, diagnosis, assessment, treatment guidance, patient management guidance or stratification will be displayed and/or printed for the user (typically a health professional such as a physician).

In one embodiment of the invention, a software system can be employed, in which a machine learning algorithm is evident, preferably to identify hospitalized patients at risk for sepsis, severe sepsis and septic shock using data from electronic health records (EHRs). A machine learning approach can be trained on a random forest classifier using EHR data (such as labs, biomarker expression, vitals, and demographics) from patients. Machine learning is a type of artificial intelligence that provides computers with the ability to learn complex patterns in data without being explicitly programmed, unlike simpler rule-based systems. Earlier studies have used electronic health record data to trigger alerts to detect clinical deterioration in general. In one embodiment of the invention the processing of proADM levels may be incorporated into appropriate software for comparison to existing data sets, for example proADM levels may also be processed in machine learning software to assist in diagnosing or prognosing the occurrence of an adverse event.

The combined employment of proADM or fragments thereof in combination with another biomarker such as PCT or CRP may be realized either in a single multiplex assay, or in two separate assays conducted on a sample form the patient. The sample may relate to the same sample, or to different samples. The assay employed for the detection and determination of proADM and for example PCT may also be the same or different, for example an immunoassay may be employed for the determination of one of the above markers. More detailed descriptions of suitable assays are provided below.

Cut-off values and other reference levels of proADM or fragments thereof in patients who have been diagnosed as being critically ill and are under treatment may be determined by previously described methods. For example, methods are known to a skilled person for using the Coefficient of variation in assessing variability of quantitative assays in order to establish reference values and/or cut-offs (George F. Reed et al., Clin Diagn Lab Immunol. 2002; 9(6):1235-1239).

Additionally, functional assay sensitivity can be determined in order to indicate statistically significant values for use as reference levels or cut-offs according to established techniques. Laboratories are capable of independently establishing an assays functional sensitivity by a clinically relevant protocol. "Functional sensitivity" can be considered as the concentration that results in a coefficient of variation (CV) of 20% (or some other predetermined % CV), and is thus a measure of an assays precision at low analyte levels. The CV is therefore a standardization of the standard deviation (SD) that allows comparison of variability estimates regardless of the magnitude of analyte concentration, at least throughout most of the working range of the assay.

Furthermore, methods based on ROC analysis can be used to determine statistically significant differences between two clinical patient groups. Receiver Operating Characteristic (ROC) curves measure the sorting efficiency of the model's fitted probabilities to sort the response levels. ROC curves can also aid in setting criterion points in diagnostic tests. The higher the curve from the diagonal, the better the fit. If the logistic fit has more than two response levels, it produces a generalized ROC curve. In such a plot, there is a curve for each response level, which is the ROC curve of that level versus all other levels. Software capable of enabling this kind of analysis in order to establish suitable reference levels and cut-offs is available, for example JMP 12, JMP 13, Statistical Discovery, from SAS.

Cut off values may similarly be determined for PCT. Literature is available to a skilled person for determining an appropriate cut-off, for example Philipp Schuetz et al. (BMC Medicine. 2011; 9:107) describe that at a cut-off of 0.1 ng/mL, PCT had a very high sensitivity to exclude infection. Terence Chan et al. (Expert Rev. Mol. Diagn. 2011; 11(5), 487.496) described that indicators such as the positive and negative likelihood ratios, which are calculated based on sensitivity and specificity, are also useful for assessing the strength of a diagnostic test. Values are commonly graphed for multiple cut-off values (CVs) as a receiver operating characteristic curve. The area under the curve value is used to determine the best diagnostically relevant CV. This literature describes the variation of CVs (cut-off values, that is dependent on the assay and study design), and suitable methods for determining cut-off values.

Population averages levels of proADM or fragments thereof may also be used as reference values, for example mean proADM population values, whereby patients that are diagnosed as critically ill may be compared to a control population, wherein the control group preferably comprises more than 10, 20, 30, 40, 50 or more subjects.

In one embodiment of the invention, the cut-off level for PCT may be a value in the range of 0.01 to 100.00 ng/ml in a serum sample, when using for example a Luminex® MAC Pix E-Bioscience Assay or the B•R•A•H•M•S PCT™ KRYPTOR® Assay. In a preferred embodiment the cut-off level of PCT may be in the range of 0.01 to 100, 0.05 to 50, 0.1 to 20, or 0.1 to 2 ng/mL, and most preferably >0.05 to 0.5 ng/mL. Any value within these ranges may be considered as an appropriate cut-off value. For example, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 6, 7, 8, 9, 10, 15, 20, 25, 30, 35, 40, 45, 50, 55, 60, 65, 70, 75, 80, 85, 90, 95 or 100 ng/ml may be employed. In some embodiments, PCT levels for healthy subjects are approximately 0.05 ng/ml.

DETAILED DESCRIPTION OF THE INVENTION

The invention relates to a method for the diagnosis, prognosis, prediction, risk assessment and/or risk stratification of a subsequent trauma-related complication in a poly-trauma patient, comprising providing a sample of said patient, wherein the sample is isolated from the patient after the severe injury, determining a level of proADM or fragment(s) thereof in said sample, wherein said level of proADM or fragment(s) thereof correlates with the likelihood of a subsequent trauma-related complication.

As is evident from the data presented herein, the likelihood of presence or absence of a trauma-related complication in a polytrauma patient is indicated by the level of proADM or fragment(s) thereof.

The present invention has the following advantages over the conventional methods: the inventive methods and the kits are fast, objective, easy to use and precise. The methods and kits of the invention relate to markers and clinical scores that are easily measurable in routine methods in hospitals, because the levels of ADM, PCT, lactate, c-reactive protein, SOFA, qSOFA, APACHE II, SAPS II can be determined in routinely obtained blood samples or further biological fluids or samples obtained from a subject.

As used herein, the "patient" or "subject" may be a vertebrate. In the context of the present invention, the term "subject" includes both humans and animals, particularly mammals, and other organisms.

In the sense of the present invention, a "polytrauma patient" is a subject who is severely injured and has suffered from a polytrauma. The term "polytrauma" relates to a condition that is associated with multiple traumata or a severe trauma. Typically, the term describes a condition of a person who has been subjected to traumatic injury, preferably more than one traumatic injuries, such as for example a serious head injury in addition to a serious burn.

The term polytrauma may also refer to injuries associated with a certain Injury Severity Score (ISS), such as an ISS greater than 12, 13, 14, 15, 16, 17, 18, 19, 20, preferably greater than 16. Polytraumata are often associated with accidents, which can involve high velocities causing multiple injuries, such as motor vehicle crashes (motorcycle crashes, car crashes). Polytrauma is commonly characterized by multiple head injuries, vision and hearing loss, nerve damage, multiple bone fractures, unhealed body wounds and infections—either of which can be life threatening. Other injuries may include severed limbs or spinal cord damage with the majority of patients experiencing some amount of traumatic brain injury.

The Injury Severity Score (ISS) is an established medical score to assess trauma and polytrauma severity (Baker S P et al. (1974). "The Injury Severity Score: a method for describing patients with multiple injuries and evaluating emergency care". The Journal of Trauma. Lippincott Williams & Wilkins. 14 (3): 187-196; Copes W S et al. (1988). "The Injury Severity Score revisited". The Journal of Trauma. Lippincott Williams & Wilkins. 28 (1): 69-77). It correlates with mortality, morbidity and hospitalization time after injury. It is used to define the term major trauma or polytrauma. A major trauma (or polytrauma) is defined as the Injury Severity Score being greater than 15, preferably greater than 16. The Abbreviated Injury Scale (AIS) is used to calculate the ISS score and is an anatomically based consensus-derived global severity scoring system that classifies each injury in every body region according to its relative severity on a six-point ordinal scale: minor—1, moderate—2, serious—3, severe—4, critical—6, maximal (currently untreatable)—7. There are nine AIS chapters corresponding to nine body regions: Head, face, neck, thorax, abdomen, spine, upper extremity, lower extremity, external and other.

The ISS is based (see below) upon the Abbreviated Injury Scale (AIS) and to calculate an ISS for an injured person, the body is divided into six ISS body regions: Head or neck—including cervical spine; face—including the facial skeleton, nose, mouth, eyes and ears; chest—thoracic spine and diaphragm; abdomen or pelvic contents—abdominal organs and lumbar spine; extremities or pelvic girdle—pelvic skeleton; external. To calculate an ISS, the highest AIS severity code is taken in each of the three most severely injured ISS body regions, each AIS code is squared and the three squared numbers are added for an ISS ($ISS=A^2+B^2+C^2$, wherein A, B, C are the AIS scores of the three most injured ISS body regions). The ISS scores ranges from 1 to 75 (i.e. AIS scores of 5 for each category). If any of the three scores is a 6, the score is automatically set at 75, since a score of 6 ("unsurvivable") indicates the futility of further medical care in preserving life.

In embodiments of the invention, the polytrauma patients include burn patients that qualify as polytrauma patients. Such burn patients either have an ISS score of equal or more than 17 or have at least one additional trauma in addition to the burn. In embodiments, polytrauma patients do not comprise burn patients with an ISS of less than 17, and/or burn patients that have no coexisting polytrauma and have a burned total body surface area (TBSA) below 40%, preferably below 39%, below 38%, below 37% or below 36%.

Initial management/treatment and diagnosis of poly-trauma patients is usually provided in the Emergency Department (ED). The time needed for a trauma patient's evaluation in the ED is called time-to-treatment. On admission to hospital or another institution providing medical service a trauma patient should immediately undergo thorough examination, including x-ray diagnosis of their cervical spine, chest, and pelvis, commonly known as a 'trauma series', to ascertain possible life-threatening injuries. Examples would be a fractured cervical vertebra, a severely fractured pelvis, or a haemothorax. Once this initial survey is complete, x-rays may be taken of the limbs to assess the possibility of other fractures. It also is quite common in severe trauma for patients to be sent directly to CT or a surgery theatre, if they require emergency treatment. Less obvious signs of polytrauma may include difficulties with attention, concentration and memory, headaches, ringing in the ears, light-headedness, irritability and impaired decision making.

Treatment of polytrauma patients may involve a "damage control" orthopedic surgery, which may involve treatment of long bone fractures, the early restoration of the "lethal triad" of persistent metabolic acidosis, hypothermia, and coagulopathy represents the prime goal for survival, transfer of the patient to the ICU at the earliest time point after stabilization of vital functions for restoration of physiological parameters, avoidance of prolonged surgical interventions to prevent a lethal "second hit" in these patients. Treatment of polytrauma patients may include four distinct phases of assessment and management, (1) life-saving surgery with early recognition of those trauma patients that warrant damage control ("ground zero" recognition phase); (2) salvage operation for control of hemorrhage and contamination ("OR phase"); (3) intensive care management for restoration of physiological and immunologic baseline functions ("ICU phase"); (4) scheduled definitive surgery ("reconstructive phase"). Further measures of managing polytrauma patients are known the skilled person and have been summarized multiple time in the literature, for example by Stahel P F et al. (Stahel P F et al. "Current Concepts of Polytrauma Management". European Journal of Trauma 2005; 31:200-11).

In the context of the present invention, a "trauma-related complication" or an "adverse event" in the health of a polytrauma patient relates to events that indicate complications or worsening of the health state of the polytrauma patient, which may be due to the event of polytrauma. Such trauma-related complications may lead to dysfunction or failure of remote—primarily not injured—organs and vital systems. Such adverse events include, without limitation, death of the patient and death of a patient within 28 days after the polytrauma, postoperative pulmonary compromise, venous thrombosis/pulmonary embolism, cellulitis or decubitus ulcer, postprocedural hemorrhage or hematoma, postoperative pneumonia, reopening of surgical site, wound infection, postoperative infections, postoperative infections not pneumonia/wound, postoperative GI hemorrhage or ulceration, postoperative stroke, postoperative AMI, postoperative cardiac abnormality, shock or cardiorespiratory arrest, aspiration pneumonia, postoperative urinary tract complication, postoperative physical and metabolic derangements, central or peripheral nervous system, complications related to anesthetic agents/CNS agents.

Trauma-related complications can be divided into infection-related and non-infection related complications. Furthermore, examples of adverse events and trauma-related complications include situations where a deterioration of clinical symptoms indicates the requirement for therapeutic measures, such as a focus cleaning procedure, transfusion of blood products, infusion of colloids, invasive mechanical ventilation, non-invasive mechanical ventilation, emergency surgery, organ replacement therapy, such as renal or liver replacement, and vasopressor therapy. Infection-related complication comprise, without limitation, occurrence of an infection or a new infection, a nosocomial infection, sepsis, septic shock and/or septicemia.

Non-infection-related complication comprise, without limitation, rhabdomyolysis, organ failure and deterioration of the patient's general clinical signs or symptoms, such as hypotension or hypertension, tachycardia or bradycardia. In embodiments, the term trauma-related complications may explicitly not relate to conditions or parameters that are the consequence of a trauma-related complication. For example, changes in the extracellular volume status, the fluid balance, the salt balance and/or the globular volume status of a patient may not qualify as a trauma-related complication since such changes can also represent an improvement of the patient's status and therefore are not a complication per se. Furthermore, such changes may not be regarded themselves as a complication, but rather as the consequence of a complication. For example, kidney failure or infectious diseases or sepsis, which can be regarded as a trauma-related complication in the sense of the invention, may lead to fluid imbalance. Accordingly, in embodiments the method of the present invention does not relate to the diagnosis, prognosis, prediction, risk assessment and/or risk stratification of changes in the extracellular volume status, the fluid balance, the salt balance and/or the globular volume status of a patient.

Rhabdomyolysis is a condition in which damaged skeletal muscle breaks down rapidly. Symptoms include muscle pains, weakness, vomiting, and confusion, dark (or "tea-colored") urine and/or an irregular heartbeat. Some of the muscle breakdown products, such as the protein myoglobin, are harmful to the kidneys and may lead to kidney failure.

A diagnosis of rhabdomyolysis may be suspected in anyone who has suffered trauma, crush injury or prolonged immobilization, but it may also be identified at a later stage due to deteriorating kidney function (abnormally raised or increasing creatinine and urea levels, falling urine output) or reddish-brown discoloration of the urine. A reliable diagnostic test for rhabdomyolysis is the level of creatine kinase (CK) in the blood. CK is released by damaged muscle, and levels above 1000 U/L (5 times the upper limit of normal (ULN)) indicate rhabdomyolysis) and more than 5,000 U/L indicate severe disease but depending on the extent of the rhabdomyolysis, concentrations up to 100,000 U/I are not unusual. CK concentrations usually rise steadily for 12 hours after the original muscle injury, remain elevated for 1-3 days and then fall gradually. Detection of elevated myoglobin levels in blood or urine can be used in the diagnosis of rhabdomyolysis and is associated with a higher risk of kidney impairment. Elevated concentrations of the enzyme lactate dehydrogenase (LDH) are also indicative of rhabdomyolysis, as well as markers of muscle damage, such as aldolase, troponin, carbonic anhydrase type 3 and fatty acid-binding protein (FABP). Furthermore, transaminases are also usually increased in rhabdomyolysis. Further diagnostic markers that can be used in the detection of rhabdomyolysis include high potassium levels, electrocardiography (ECG) (which may show whether the elevated potassium levels are affecting the conduction system of the heart), low calcium levels.

The treatment of rhabdomyolysis may comprise administration of large quantities of intravenous fluids, dialysis or hemofiltration, administration of sodium bicarbonate, mannitol, calcium, insulin and/or salbutamol.

The polytrauma patient described herein can be at the emergency department or intensive care unit or in specialized clinical sites such as major trauma centres or in other point of care settings, such as in an emergency transporter, such as an ambulance, or at a general practitioner, who is confronted with a patient with said symptoms.

The term "ICU-patient" patient relates, without limitation, a patient who has been admitted to an intensive care unit. An intensive care unit can also be termed an intensive therapy unit or intensive treatment unit (ITU) or critical care unit (CCU), is a special department of a hospital or health care facility that provides intensive treatment medicine. ICU-patients usually suffer from severe and life-threatening illnesses and injuries, which require constant, close monitoring and support from specialist equipment and medications in order to ensure normal bodily functions. Common conditions that are treated within ICUs include, without limitation, polytrauma, acute or adult respiratory distress syndrome (ARDS), trauma, organ failure and sepsis.

As used herein, "diagnosis" in the context of the present invention relates to the recognition and (early) detection of a clinical condition of a subject linked to a polytrauma. Also the assessment of the severity of the polytrauma may be encompassed by the term "diagnosis".

"Prognosis" relates to the prediction of an outcome or a specific risk for a subject based on a polytrauma. This may also include an estimation of the chance of recovery or the chance of an adverse outcome for said subject.

The methods of the invention may also be used for monitoring, therapy monitoring, therapy guidance and/or therapy control. "Monitoring" relates to keeping track of a polytrauma patient and potentially occurring complications, e.g. to analyze the progression of the healing process or the influence of a particular treatment or therapy on the health state of the polytrauma patient.

The term "therapy monitoring" or "therapy control" in the context of the present invention refers to the monitoring and/or adjustment of a therapeutic treatment of said polytrauma patient, for example by obtaining feedback on the efficacy of the therapy. As used herein, the term "therapy guidance" refers to application of certain therapies, therapeutic actions or medical interventions based on the value/level of one or more biomarkers and/or clinical parameter and/or clinical scores. This includes the adjustment of a therapy or the discontinuation of a therapy.

In the present invention, the terms "risk assessment" and "risk stratification" relate to the grouping of subjects into different risk groups according to their further prognosis. Risk assessment also relates to stratification for applying preventive and/or therapeutic measures. The term "therapy stratification" in particular relates to grouping or classifying patients into different groups, such as risk groups or therapy groups that receive certain differential therapeutic measures depending on their classification. The term "therapy stratification" also relates to grouping or classifying patients with infections or having symptoms of an infectious disease into a group that are not in need to receive certain therapeutic measures.

It is understood that in the context of the present invention "determining the level of proADM or fragment(s) thereof" or the like refers to any means of determining proADM or a fragment thereof. The fragment can have any length, e.g. at least about 5, 10, 20, 30, 40, 50 or 100 amino acids, so long as the fragment allows the unambiguous determination of the level of proADM or fragment thereof. In particular preferred aspects of the invention, "determining the level of proADM" refers to determining the level of midregional proadrenomedullin (MR-proADM). MR-proADM is a fragment and/or region of proADM.

The peptide adrenomedullin (ADM) was discovered as a hypotensive peptide comprising 52 amino acids, which had been isolated from a human phenochromocytome (Kitamura et al., 1993). Adrenomedullin (ADM) is encoded as a precursor peptide comprising 185 amino acids ("preproadrenomedullin" or "pre proADM"). An exemplary amino acid sequence of ADM is given in SEQ ID NO: 1.

```
SEQ ID NO: 2: amino acid sequence of MR-pro-ADM
(AS 45-92 of pre-pro-ADM):
ELRMSSSYPT GLADVKAGPA QTLIRPQDMK GASRSPEDSS
PDAARIRV
```

It is also envisaged herein that a peptide and fragment thereof of pre-proADM or MR-proADM can be used for the herein described methods. For example, the peptide or the fragment thereof can comprise the amino acids 22-41 of pre-proADM (PAMP peptide) or amino acids 95-146 of pre-proADM (mature adrenomedullin, including the biologically active form, also known as bio-ADM). A C-terminal fragment of proADM (amino acids 153 to 185 of pre proADM) is called adrenotensin. Fragments of the proADM peptides or fragments of the MR-proADM can comprise, for example, at least about 5, 10, 20, 30 or more amino acids. Accordingly, the fragment of proADM may, for example, be selected from the group consisting of MR-proADM, PAMP, adrenotensin and mature adrenomedullin, preferably herein the fragment is MR-proADM.

The determination of these various forms of ADM or proADM and fragments thereof also encompass measuring and/or detecting specific sub-regions of these molecules, for example by employing antibodies or other affinity reagents directed against a particular portion of the molecules, or by determining the presence and/or quantity of the molecules by measuring a portion of the protein using mass spectrometry.

Accordingly, the methods and kits of the present invention can also comprise determining at least one further biomarker, marker, clinical score and/or parameter in addition to ADM.

As used herein, a parameter is a characteristic, feature, or measurable factor that can help in defining a particular system. A parameter is an important element for health- and physiology-related assessments, such as a disease/disorder/clinical condition risk, preferably organ dysfunction(s). Furthermore, a parameter is defined as a characteristic that is objectively measured and evaluated as an indicator of normal biological processes, pathogenic processes, or pharmacologic responses to a therapeutic intervention. An exemplary parameter can be selected from the group consisting of Acute Physiology and Chronic Health Evaluation II (APACHE II), the simplified acute physiology score (SAPSII score), sequential organ failure assessment score (SOFA score), quick sequential organ failure assessment score (qSOFA), body mass index, weight, age, sex, IGS II, liquid intake, white blood cell count, sodium, potassium,

```
SEQ ID NO: 1: amino acid sequence of pre-pro-ADM:
  1  MKLVSVALMY LGSLAFLGAD TARLDVASEF RKKWNKWALS RGKRELRMSS

51  SYPTGLADVK AGPAQTLIRP QDMKGASRSP EDSSPDAARI RVKRYRQSMN

101  NFQGLRSFGC RFGTCTVQKL AHQIYQFTDK DKDNVAPRSK ISPQGYGRRR

151  RRSLPEAGPG RTLVSSKPQA HGAPAPPSGS APHFL
```

ADM comprises the positions 95-146 of the pre-proADM amino acid sequence and is a splice product thereof. "Proadrenomedullin" ("proADM") refers to pre-proADM without the signal sequence (amino acids 1 to 21), i.e. to amino acid residues 22 to 185 of pre-proADM. "Midregional proadrenomedullin" ("MR-proADM") refers to the amino acids 42 to 95 of pre-proADM. An exemplary amino acid sequence of MR-proADM is given in SEQ ID NO: 2.

temperature, blood pressure, dopamine, bilirubin, respiratory rate, partial pressure of oxygen, World Federation of Neurosurgical Societies (WFNS) grading, and Glasgow Coma Scale (GCS).

As used herein, terms such as "marker", "surrogate", "prognostic marker", "factor" or "biomarker" or "biological marker" are used interchangeably and relate to measurable and quantifiable biological markers (e.g., specific protein or enzyme concentration or a fragment thereof, specific hormone concentration or a fragment thereof, or presence of biological substances or a fragment thereof) which serve as indices for health- and physiology-related assessments, such as a disease/disorder/clinical condition risk, preferably an adverse event. A marker or biomarker is defined as a characteristic that can be objectively measured and evaluated as an indicator of normal biological processes, pathogenic processes, or pharmacologic responses to a therapeutic intervention. Biomarkers may be measured in a sample (as a blood, plasma, urine, or tissue test).

The at least one further marker and/or parameter of said subject can be selected from the group consisting of a level of lactate in said sample, a level of procalcitonin (PCT) in said sample, the sequential organ failure assessment score (SOFA score) of said subject, the simplified acute physiology score (SAPSII) of said subject, the Acute Physiology and Chronic Health Evaluation II (APACHE II) score of said subject and a level of the soluble fms-like tyrosine kinase-1 (sFlt-1), Histone H2A, Histone H2B, Histone H3, Histone H4, calcitonin, Endothelin-1 (ET-1), Arginine Vasopressin (AVP), Atrial Natriuretic Peptide (ANP), Neutrophil Gelatinase-Associated Lipocalin (NGAL), Troponin, Brain Natriuretic Peptide (BNP), C-Reactive Protein (CRP), Pancreatic Stone Protein (PSP), Triggering Receptor Expressed on Myeloid Cells 1 (TREM1), Interleukin-6 (IL-6), Interleukin-1, Interleukin-24 (IL-24), Interleukin-22 (IL-22), Interleukin (IL-20) other ILs, Presepsin (sCD14-ST), Lipopolysaccharide Binding Protein (LBP), Alpha-1-Antitrypsin, Matrix Metalloproteinase 2 (MMP2), Metalloproteinase 2 (MMP8), Matrix Metalloproteinase 9 (MMP9), Matrix Metalloproteinase 7 (MMP7, Placental growth factor (PlGF), Chromogranin A, 5100A protein, 5100B protein and Tumor Necrosis Factor α (TNFα), Neopterin, Alpha-1-Antitrypsin, pro-arginine vasopressin (AVP, proAVP or Copeptin), procalcitonin, atrial natriuretic peptide (ANP, pro-ANP), Endothelin-1, E-selectin, ICAM-1, VCAM-1, IP-10, CCL1/TCA3, CCL11, CCL12/MCP-5, CCL13/MCP-4, CCL14, CCL15, CCL16, CCL17/TARC, CCL18, CCL19, CCL2/MCP-1, CCL20, CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CX3CL1, CXCL1, CXCL10, CXCL11, CXCL12, CXCL13, CXCL14, CXCL15, CXCL16, CXCL17, CXCL2/MIP-2, CXCL3, CXCL4, CXCL5, CXCL6, CXCL7/Ppbp, CXCL9, IL8/CXCL8, XCL1, XCL2, FAM19A1, FAM19A2, FAM19A3, FAM19A4, FAM19A5, CLCF1, CNTF, IL11, IL31, IL6, Leptin, LIF, 05M, IFNA1, IFNA10, IFNA13, IFNA14, IFNA2, IFNA4, IFNA7, IFNB1, IFNE, IFNG, IFNZ, IFNA8, IFNA5/IFNaG, IFNω/IFNW1, BAFF, 4-1BBL, TNFSF8, CD40LG, CD70, CD95L/CD178, EDA-A1, TNFSF14, LTA/TNFB, LTB, TNFa, TNFSF10, TNFSF11, TNFSF12, TNFSF13, TNFSF15, TNFSF4, 1L18, IL18BP, IL1A, IL1B, IL1F10, IL1F3/IL1RA, IL1F5, IL1F6, IL1F7, IL1F8, IL1RL2, IL1F9, IL33 or a fragment thereof.

As used herein, "procalcitonin" or "PCT" relates to a peptide spanning amino acid residues 1-116, 2-116, 3-116, or fragments thereof, of the procalcitonin peptide. PCT is a peptide precursor of the hormone calcitonin. Thus the length of procalcitonin fragments is at least 12 amino acids, preferably more than 50 amino acids, more preferably more than 110 amino acids. PCT may comprise post-translational modifications such as glycosylation, liposidation or derivatization. Procalcitonin is a precursor of calcitonin and katacalcin. Thus, under normal conditions the PCT levels in the circulation are very low (<about 0.05 ng/ml).

The level of PCT in the sample of the subject can be determined by immunoassays as described herein. As used herein, the level of ribonucleic acid or deoxyribonucleic acids encoding "procalcitonin" or "PCT" can also be determined. Methods for the determination of PCT are known to a skilled person, for example by using products obtained from Thermo Fisher Scientific/B•R•A•H•M•S GmbH.

Lactate, or lactic acid, is an organic compound with the formula $CH_3CH(OH)COOH$, which occurs in bodily fluids including blood. Blood tests for lactate are performed to determine the status of the acid base homeostasis in the body. Lactic acid is a product of cell metabolism that can accumulate when cells lack sufficient oxygen (hypoxia) and must turn to a less efficient means of energy production, or when a condition causes excess production or impaired clearance of lactate. Lactic acidosis can be caused by an inadequate amount of oxygen in cells and tissues (hypoxia), for example if someone has a condition that may lead to a decreased amount of oxygen delivered to cells and tissues, such as shock, septic shock or congestive heart failure, the lactate test can be used to help detect and evaluate the severity of hypoxia and lactic acidosis.

C-reactive protein (CRP) is a pentameric protein, which can be found in bodily fluids such as blood plasma. CRP levels can rise in response to inflammation. Measuring and charting CRP values can prove useful in determining disease progress or the effectiveness of treatments.

As used herein, the "sequential organ failure assessment score" or "SOFA score" is one score used to track a patient's status during the stay in an intensive care unit (ICU). The SOFA score is a scoring system to determine the extent of a person's organ function or rate of failure. The score is based on six different scores, one each for the respiratory, cardiovascular, hepatic, coagulation, renal and neurological systems. Both the mean and highest SOFA scores being predictors of outcome. An increase in SOFA score during the first 24 to 48 hours in the ICU predicts a mortality rate of at least 50% up to 95%. Scores less than 9 give predictive mortality at 33% while above 14 can be close to or above 95%.

As used herein, the quick SOFA score (qSOFA) is a scoring system that indicates a patient's organ dysfunction or mortality risk. The score is based on three criteria: 1) an alteration in mental status, 2) a decrease in systolic blood pressure of less than 100 mm Hg, 3) a respiration rate greater than 22 breaths per minute. Patients with two or more of these conditions are at greater risk of having an organ dysfunction or to die.

As used herein, "APACHE II" or "Acute Physiology and Chronic Health Evaluation II" is a severity-of-disease classification scoring system (Knaus et al., 1985). It can be applied within 24 hours of admission of a patient to an intensive care unit (ICU) and may be determined based on 12 different physiologic parameters: AaDO2 or PaO2 (depending on FiO2), temperature (rectal), mean arterial pressure, pH arterial, heart rate, respiratory rate, sodium (serum), potassium (serum), creatinine, hematocrit, white blood cell count and Glasgow Coma Scale.

As used herein, "SAPS II" or "Simplified Acute Physiology Score II" relates to a system for classifying the severity of a disease or disorder (see Le Gall J R et al., A new Simplified Acute Physiology Score (SAPS II) based on a European/North American multicenter study. JAMA. 1993; 270(24):2957-63.). The SAPS II score is made of 12 physiological variables and 3 disease-related variables. The point score is calculated from 12 routine physiological measurements, information about previous health status and some information obtained at admission to the ICU. The SAPS II score can be determined at any time, preferably, at day 2.

The "worst" measurement is defined as the measure that correlates to the highest number of points. The SAPS II score ranges from 0 to 163 points. The classification system includes the followings parameters: Age, Heart Rate, Systolic Blood Pressure, Temperature, Glasgow Coma Scale, Mechanical Ventilation or CPAP, PaO2, FiO2, Urine Output, Blood Urea Nitrogen, Sodium, Potassium, Bicarbonate, Bilirubin, White Blood Cell, Chronic diseases and Type of admission. There is a sigmoidal relationship between mortality and the total SAPS II score. The mortality of a subject is 10% at a SAPSII score of 29 points, the mortality is 25% at a SAPSII score of 40 points, the mortality is 50% at a SAPSII score of 52 points, the mortality is 75% at a SAPSII score of 64 points, the mortality is 90% at a SAPSII score of 77 points (Le Gall loc. cit.).

As used herein, the term "sample" is a biological sample that is obtained or isolated from the patient or subject. "Sample" as used herein may, e.g., refer to a sample of bodily fluid or tissue obtained for the purpose of analysis, diagnosis, prognosis, or evaluation of a subject of interest, such as a patient. Preferably herein, the sample is a sample of a bodily fluid, such as blood, serum, plasma, cerebrospinal fluid, urine, saliva, sputum, pleural effusions, cells, a cellular extract, a tissue sample, a tissue biopsy, a stool sample and the like. Particularly, the sample is blood, blood plasma, blood serum, or urine.

Embodiments of the present invention refer to the isolation of a first sample and the isolation of a second sample. In the context of the method of the present invention, the terms "first sample" and "second sample" relate to the relative determination of the order of isolation of the samples employed in the method of the present invention. When the terms first sample and second sample are used in specifying the present method, these samples are not to be considered as absolute determinations of the number of samples taken. Therefore, additional samples may be isolated from the patient before, during or after isolation of the first and/or the second sample, or between the first or second samples, wherein these additional samples may or may not be used in the method of the present invention. The first sample may therefore be considered as any previously obtained sample. The second sample may be considered as any further or subsequent sample.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood), for example for at least 15 minutes at 2000 to 3000 g.

"Serum" in the context of the present invention is the liquid fraction of whole blood that is collected after the blood is allowed to clot. When coagulated blood (clotted blood) is centrifuged serum can be obtained as supernatant.

As used herein, "urine" is a liquid product of the body secreted by the kidneys through a process called urination (or micturition) and excreted through the urethra.

In embodiments of the present invention the trauma-related complication may be sepsis, severe sepsis and/or septic shock. "Sepsis" in the context of the invention refers to a systemic response to infection. Alternatively, sepsis may be seen as the combination of SIRS with a confirmed infectious process or an infection. Sepsis may be characterized as clinical syndrome defined by the presence of both infection and a systemic inflammatory response (Levy M M et al. 2001 SCCM/ESICM/ACCP/ATS/SIS International Sepsis Definitions Conference. Crit Care Med. 2003 April; 31(4):1250-6). The term "sepsis" used herein includes, but is not limited to, sepsis, severe sepsis, and septic shock.

The term "sepsis" used herein includes, but is not limited to, sepsis, severe sepsis, and septic shock. Severe sepsis in refers to sepsis associated with organ dysfunction, hypoperfusion abnormality, or sepsis-induced hypotension. Hypoperfusion abnormalities include lactic acidosis, oliguria and acute alteration of mental status. Sepsis-induced hypotension is defined by the presence of a systolic blood pressure of less than about 90 mm Hg or its reduction by about 40 mm Hg or more from baseline in the absence of other causes for hypotension (e.g. cardiogenic shock). Septic shock is defined as severe sepsis with sepsis-induced hypotension persisting despite adequate fluid resuscitation, along with the presence of hypoperfusion abnormalities or organ dysfunction (Bone et al., CHEST 101(6): 1644-55, 1992).

The term sepsis may alternatively be defined as life-threatening organ dysfunction caused by a dysregulated host response to infection. For clinical operationalization, organ dysfunction can preferably be represented by an increase in the Sequential Organ Failure Assessment (SOFA) score of 2 points or more, which is associated with an in-hospital mortality greater than 10%. Septic shock may be defined as a subset of sepsis in which particularly profound circulatory, cellular, and metabolic abnormalities are associated with a greater risk of mortality than with sepsis alone. Patients with septic shock can be clinically identified by a vasopressor requirement to maintain a mean arterial pressure of 65 mm Hg or greater and serum lactate level greater than 2 mmol/L (>18 mg/dL) in the absence of hypovolemia.

The term "sepsis" used herein relates to all possible stages in the development of sepsis. The term "sepsis" also includes severe sepsis or septic shock based on the SEPSIS-2 definition (Bone et al., 2009). The term "sepsis" also includes subjects falling within the SEPSIS-3 definition (Singer et al., 2016). The term "sepsis" used herein relates to all possible stages in the development of sepsis.

As used herein, "infection" within the scope of the invention means a pathological process caused by the invasion of normally sterile tissue or fluid by pathogenic or potentially pathogenic agents/pathogens, organisms and/or microorganisms, and relates preferably to infection(s) by bacteria, viruses, fungi, and/or parasites. Accordingly, the infection can be a bacterial infection, viral infection, and/or fungal infection. The infection can be a local or systemic infection. For the purposes of the invention, a viral infection may be considered as infection by a microorganism.

Furthermore, the infection-related complication can be a "nosocomial" infection. Nosocomial infections are also called hospital-acquired infections (HAI) are infections that are acquired in a hospital or other health care facility. To emphasize both hospital and nonhospital settings, it is sometimes instead called a health care-associated infection (HAI or HCAI). Such an infection can be acquired in hospital, nursing home, rehabilitation facility, outpatient clinic, or other clinical settings. Nosocomial infection may be spread to the susceptible patient in the clinical setting by various means. Health care staff can spread infection, in addition to contaminated equipment, bed linens, or air droplets. The infection can originate from the outside environment, another infected patient, staff that may be infected, or in some cases, the source of the infection cannot be determined. In some cases the microorganism originates from the patient's own skin microbiota, becoming opportunistic after surgery or other procedures that compromise the protective skin barrier. Though the patient may have contracted the infection from their own skin, the infection is still considered nosocomial since it develops in the health care setting.

Further, the subject suffering from an infection can suffer from more than one source(s) of infection simultaneously. For example, the subject suffering from an infection can suffer from a bacterial infection and viral infection; from a viral infection and fungal infection; from a bacterial and fungal infection, and from a bacterial infection, fungal infection and viral infection, or suffer from a mixed infection comprising one or more of the infections listed herein, including potentially a superinfection, for example one or more bacterial infections in addition to one or more viral infections and/or one or more fungal infections.

As used herein "infectious disease" comprises all diseases or disorders that are associated with bacterial and/or viral and/or fungal infections.

According to the present invention, polytrauma patients may need a very strict control, with respect of vital functions and/or monitoring of organ protection and may be under medical treatment.

In the context of the present invention, the term "medical treatment" or "treatment" comprises various treatments and therapeutic strategies, which comprise, without limitation, anti-inflammatory strategies, administration of ADM-antagonists such as therapeutic antibodies, si-RNA or DNA, the extracorporal blood purification or the removal of harmful substances via apheresis, dialyses, adsorbers to prevent the cytokine storm, removal of inflammatory mediators, plasma apheresis, administration of vitamines such as vitamin C, surgery, emergency surgery, ventilation like mechanical ventilation and non-mechanical ventilation, to provide the body with sufficient oxygen, for example, focus cleaning procedures, transfusion of blood products, infusion of colloids, organ replacement, such as renal or liver replacement, antibiotic treatment, invasive mechanical ventilation, non-invasive mechanical ventilation, vasopressor use, fluid therapy, apheresis and measures for organ protection.

Further treatments of the present invention comprise the administration of cells or cell products like stem cells, blood or plasma, and the stabilization of the patients circulation and the protection of endothelial glycocalyx, for example via optimal fluid management strategies, for example to reach normovolemia and prevent or treat hypervolemia or hypovolemia. Moreover, vasopressors or e.g. catecholamine as well as albumin or heparanase inhibition via unfractionated heparin or N-desulfated re-N-acetylated heparin are useful treatments to support the circulation and endothelial layer.

Additionally, medical treatments of the present invention comprise, without limitation, stabilization of the blood clotting, anti-fibrinolytic treatment, iNOS inhibitors, anti-inflammatory agents like hydrocortisone, sedatives and analgetics as well as insuline.

Artificial and mechanical ventilation are effective approaches to enhance proper gas exchange and ventilation and aim to save life during severe hypoxemia. Artificial ventilation relates to assisting or stimulating respiration of the subject. Artificial ventilation may be selected from the group consisting of mechanical ventilation, manual ventilation, extracorporeal membrane oxygenation (ECMO) and noninvasive ventilation (NIV). Mechanical ventilation relates to a method to mechanically assist or replace spontaneous breathing. This may involve a machine called a ventilator. Mechanical ventilation may be High-Frequency Oscillatory Ventilation or Partial Liquid Ventilation.

Medical treatment also comprises methods to avoid hypothermia which includes the use of warmed intravenous fluids and warm air blankets.

Medical treatment also comprises wound management including haemorrhage control, bleeding control techniques with or without tourniquets, wound cleaning, local anaesthetic application, wound closure techniques where skin adhesive strips, tissue adhesive glue, sutures, staples and wound dressings can be used.

"Fluid management" refers to the monitoring and controlling of the fluid status of a subject and the administration of fluids to stabilize the circulation or organ vitality, by e.g. oral, enteral or intravenous fluid administration. It comprises the stabilization of the fluid and electrolyte balance or the prevention or correction of hyper- or hypovolemia as well as the supply of blood products.

Surgical emergencies/Emergency surgery are needed if a subject has a medical emergency and an immediate surgical intervention may be required to preserve survival or health status. The subject in need of emergency surgery may be selected from the group consisting of subjects suffering from acute trauma, an active uncontrolled infection, organ transplantation, organ-preventive or organ-stabilizing surgery or cancer.

Cleaning Procedures are hygienic methods to prevent subjects from infections, especially nosocomial infections, comprising disinfection of all organic and inorganic surfaces that could get in contact with a patient, such as for example, skin, objects in the patient's room, medical devices, diagnostic devices, or room air. Cleaning procedures include the use of protective clothes and units, such as mouth guards, gowns, gloves or hygiene lock, and actions like restricted patient visits. Furthermore, cleaning procedures comprise the cleaning of the patient itself and the clothes or the patient.

In a preferred embodiment, the term "medical treatment" or "treatment" comprises antibiotic treatment such as intravenous antibiotic, oral antibiotics or topical antibiotics.

In the case of polytrauma patients it is very important to have an early diagnosis as well a prognosis and risk assessment of the occurrence of trauma-related complications to find the optimal therapy and patient management, since such patients are often instable and require an early therapeutic intervention in case of complication. The therapeutic approaches need to be very individual and vary from case to case. A therapeutic monitoring is needed for a best practice therapy and is influenced by the timing of treatment, the use of combined therapies and the optimization of drug dosing. A wrong or omitted therapy or management will increase the mortality rate hourly.

A medical treatment of the present invention may be an antibiotic treatment, wherein one or more "antibiotics" or "antibiotic agents" may be administered if an infection has been diagnosed or prognosed by the method of the invention. Antibiotics or antibiotic agents according to the present invention also encompass potentially the anti-fungal or anti-viral compounds used to treat a diagnosed infection or sepsis. The antibiotic agents commonly applied in the treatment of any given infection, as separated into the classes of pathogen are:

Gram positive coverage: Penicillins, (ampicillin, amoxicillin), penicillinase resistant, (Dicloxacillin, Oxacillin), Cephalosporins (1st and 2nd generation), Macrolides (Erythromycin, Clarithromycin, Azithromycin), Quinolones (gatifloxacin, moxifloxacin, levofloxacin), Vancomycin, Sulfonamide/trimethoprim, Clindamycin, Tetracyclines, Chloramphenicol, Linezolid, Synercid.

Gram negative coverage: Broad spectrum penicillins (Ticarcillin, clavulanate, piperacillin, tazobactam), Cephalosporins (2nd, 3rd, and 4th generation), Aminoglycosides, Macrolides, Azithromycin, Quinolones (Ciprofloxacin), Monobactams (Azetreonam), Sulfonamide/trimethoprim, Carbapenems (Imipenem), Chloramphenicol.

Pseudomonas coverage: Ciprofloxacin, Aminoglycosides, Some 3rd generation cephalosporins, 4th generation cephalosporins, Broad spectrum penicillins, Carbapenems.

Fungal treatments: Allyamines, Amphotericin B, Fluconazole and other Azoles, itraconazole, voriconazole, posaconazole, ravuconazole, echinocandins, Flucytosine, sordarins, chitin synthetase inhibitors, topoisomerase inhibitors, lipopeptides, pradimycins, Liposomal nystatin, Voriconazole, Echinocanidins, Imidazole, Triazole, Thiazole, Polyene.

Anti-viral treatments: Abacavir, Acyclovir (Aciclovir), activated caspase oligomerizer, Adefovir, Amantadine, Amprenavir (Agenerase), Ampligen, Arbidol, Atazanavir, Atripla, Balavir, Cidofovir, Combivir, Dolutegravir, Darunavir, Delavirdine, Didanosine, Double-stranded RNA, Docosanol, Edoxudine, Efavirenz, Emtricitabine, Enfuvirtide, Entecavir, Ecoliever, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Morpholinos, Nelfinavir, Nevirapine, Nexavir, Nitazoxanide, Nucleoside analogues, Novir, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Ribozymes, Rifampicin, Rimantadine, Ritonavir, RNase H, protease inhibitors, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine.

Furthermore, antibiotic agents comprise bacteriophages for treatment of bacterial infections, synthetic antimicrobial peptides or iron-antagonists/iron chelator. Also, therapeutic antibodies or antagonist against pathogenic structures like anti-VAP-antibodies, anti-resistant clone vaccination, administration of immune cells, such as in vitro primed or modulated T-effector cells, are antibiotic agents that represent treatment options for critically ill patients, such as sepsis patients. Further antibiotic agents/treatments or therapeutic strategies against infection or for the prevention of new infections include the use of antiseptics, decontamination products, anti-virulence agents like liposomes, sanitation, wound care, surgery.

It is also possible to combine several of the aforementioned antibiotic agents or treatments strategies.

According to the present invention ADM and optionally PCT and/or other markers or clinical scores are employed as markers for diagnosis, prognosis, prediction, risk assessment and/or risk stratification of a subsequent trauma-related complication in a polytrauma patient.

A skilled person is capable of obtaining or developing means for the identification, measurement, determination and/or quantification of any one of the above ADM molecules, or fragments or variants thereof, as well as the other markers of the present invention according to standard molecular biological practice.

The level of proADM or fragments thereof as well as the levels of other markers of the present invention can be determined by any assay that reliably determines the concentration of the marker. Particularly, mass spectrometry (MS) and/or immunoassays can be employed as exemplified in the appended examples. As used herein, an immunoassay is a biochemical test that measures the presence or concentration of a macromolecule/polypeptide in a solution through the use of an antibody or antibody binding fragment or immunoglobulin.

Methods of determining ADM or other the markers such as PCT used in the context of the present invention are intended in the present invention. By way of example, a method may be employed selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analyzers.

Determination of ADM and optionally other markers based on antibody recognition is a preferred embodiment of the invention. As used herein, the term, "antibody" refers to immunoglobulin molecules and immunologically active portions of immunoglobulin (Ig) molecules, i.e., molecules that contain an antigen binding site that specifically binds (immuno reacts with) an antigen. According to the invention, the antibodies may be monoclonal as well as polyclonal antibodies. Particularly, antibodies that are specifically binding to at least proADM or fragments thereof are used.

An antibody is considered to be specific, if its affinity towards the molecule of interest, e.g. ADM, or the fragment thereof is at least 50-fold higher, preferably 100-fold higher, most preferably at least 1000-fold higher than towards other molecules comprised in a sample containing the molecule of interest. It is well known in the art how to develop and to select antibodies with a given specificity. In the context of the invention, monoclonal antibodies are preferred. The antibody or the antibody binding fragment binds specifically to the herein defined markers or fragments thereof. In particular, the antibody or the antibody binding fragment binds to the herein defined peptides of ADM. Thus, the herein defined peptides can also be epitopes to which the antibodies specifically bind. Further, an antibody or an antibody binding fragment is used in the methods and kits of the invention that binds specifically to ADM or proADM, particularly to MR-proADM.

Further, an antibody or an antibody binding fragment is used in the methods and kits of the invention that binds specifically to proADM or fragments thereof and optionally to other markers of the present inventions such as PCT. Exemplary immunoassays can be luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, rare cryptate assay. Further, assays suitable for point-of-care testing and rapid test formats such as for instance immune-chromatographic strip tests can be employed. Automated immunoassays are also intended, such as the KRYPTOR® assay.

Alternatively, instead of antibodies, other capture molecules or molecular scaffolds that specifically and/or selectively recognize ADM may be encompassed by the scope of the present invention. Herein, the term "capture molecules"

or "molecular scaffolds" comprises molecules which may be used to bind target molecules or molecules of interest, i.e. analytes (e.g. ADM, proADM, MR-proADM, and PCT), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may, for instance, be mediated by ionic, van-der-Waals, pi-pi, sigma-pi, hydrophobic or hydrogen bond interactions or a combination of two or more of the aforementioned interactions or covalent interactions between the capture molecules or molecular scaffold and the target molecules or molecules of interest. In the context of the present invention, capture molecules or molecular scaffolds may for instance be selected from the group consisting of a nucleic acid molecule, a carbohydrate molecule, a PNA molecule, a protein, a peptide and a glycoprotein. Capture molecules or molecular scaffolds include, for example, aptamers, DARpins (Designed Ankyrin Repeat Proteins). Affimers and the like are included.

In certain aspects of the invention, the method is an immunoassay comprising the steps of:

a) contacting the sample with i. a first antibody or an antigen-binding fragment or derivative thereof specific for a first epitope of said proADM, and ii. a second antibody or an antigen-binding fragment or derivative thereof specific for a second epitope of said proADM; and b) detecting the binding of the two antibodies or antigen-binding fragments or derivates thereof to said proADM.

Preferably, one of the antibodies can be labeled and the other antibody can be bound to a solid phase or can be bound selectively to a solid phase. In a particularly preferred aspect of the assay, one of the antibodies is labeled while the other is either bound to a solid phase or can be bound selectively to a solid phase. The first antibody and the second antibody can be present dispersed in a liquid reaction mixture, and wherein a first labeling component which is part of a labeling system based on fluorescence or chemiluminescence extinction or amplification is bound to the first antibody, and a second labeling component of said labeling system is bound to the second antibody so that, after binding of both antibodies to said proADM or fragments thereof to be detected, a measurable signal which permits detection of the resulting sandwich complexes in the measuring solution is generated. The labeling system can comprise a rare earth cryptate or chelate in combination with a fluorescent or chemiluminescent dye, in particular of the cyanine type.

In a preferred embodiment, the method is executed as heterogeneous sandwich immunoassay, wherein one of the antibodies is immobilized on an arbitrarily chosen solid phase, for example, the walls of coated test tubes (e.g. polystyrol test tubes; coated tubes; CT) or microtiter plates, for example composed of polystyrol, or to particles, such as for instance magnetic particles, whereby the other antibody has a group resembling a detectable label or enabling for selective attachment to a label, and which serves the detection of the formed sandwich structures. A temporarily delayed or subsequent immobilization using suitable solid phases is also possible.

The method according to the present invention can furthermore be embodied as a homogeneous method, wherein the sandwich complexes formed by the antibody/antibodies and the marker, ADM or a fragment thereof, which is to be detected remains suspended in the liquid phase. In this case it is preferred, that when two antibodies are used, both antibodies are labeled with parts of a detection system, which leads to generation of a signal or triggering of a signal if both antibodies are integrated into a single sandwich. Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733, EP0180492 or EP0539477 and the prior art cited therein. In this way, measurements in which only reaction products comprising both labeling components in a single immune-complex directly in the reaction mixture are detected, become possible. For example, such technologies are offered under the brand names TRACE® (Time Resolved Amplified Cryptate Emission) technology or KRYPTOR® assay, implementing the teachings of the above-cited applications. Therefore, in particular preferred aspects, a diagnostic device is used to carry out the herein provided method. For example, the level of proADM or fragments thereof and/or the level of any further marker of the herein provided method, such as PCT, is determined. In particular preferred aspects, the diagnostic device is KRYPTOR® assay.

The level of the marker of the present invention, e.g. the proADM or fragments thereof, PCT or fragments thereof, or other markers, can also be determined by a mass spectrometric (MS) based methods. Such a method may comprise detecting the presence, amount or concentration of one or more modified or unmodified fragment peptides of e.g. ADM or the PCT in said biological sample or a protein digest (e.g. tryptic digest) from said sample, and optionally separating the sample with chromatographic methods, and subjecting the prepared and optionally separated sample to MS analysis. For example, selected reaction monitoring (SRM), multiple reaction monitoring (MRM) or parallel reaction monitoring (PRM) mass spectrometry may be used in the MS analysis, particularly to determine the amounts of proADM or fragments thereof.

Herein, the term "mass spectrometry" or "MS" refers to an analytical technique to identify compounds by their mass. In order to enhance the mass resolving and mass determining capabilities of mass spectrometry, the samples can be processed prior to MS analysis. Accordingly, the invention relates to MS detection methods that can be combined with immuno-enrichment technologies, methods related to sample preparation and/or chromatographic methods, preferably with liquid chromatography (LC), more preferably with high performance liquid chromatography (HPLC) or ultra high performance liquid chromatography (UHPLC). Sample preparation methods comprise techniques for lysis, fractionation, digestion of the sample into peptides, depletion, enrichment, dialysis, desalting, alkylation and/or peptide reduction. However, these steps are optional. The selective detection of analyte ions may be conducted with tandem mass spectrometry (MS/MS). Tandem mass spectrometry is characterized by mass selection step (as used herein, the term "mass selection" denotes isolation of ions having a specified m/z or narrow range of m/z's), followed by fragmentation of the selected ions and mass analysis of the resultant product (fragment) ions.

The skilled person is aware how quantify the level of a marker in the sample by mass spectrometric methods. For example, relative quantification "rSRM" or absolute quantification can be employed as described above.

Moreover, the levels (including reference levels) can be determined by mass spectrometric based methods, such as methods determining the relative quantification or determining the absolute quantification of the protein or fragment thereof of interest.

Relative quantification "rSRM" may be achieved by:

1. Determining increased or decreased presence of the target protein by comparing the SRM (Selected reaction monitoring) signature peak area from a given target fragment peptide detected in the sample to the same SRM signature peak area of the target fragment peptide in at least a second, third, fourth or more biological samples.

2. Determining increased or decreased presence of target protein by comparing the SRM signature peak area from a given target peptide detected in the sample to SRM signature peak areas developed from fragment peptides from other proteins, in other samples derived from different and separate biological sources, where the SRM signature peak area comparison between the two samples for a peptide fragment are normalized for e.g. to amount of protein analyzed in each sample.

3. Determining increased or decreased presence of the target protein by comparing the SRM signature peak area for a given target peptide to the SRM signature peak areas from other fragment peptides derived from different proteins within the same biological sample in order to normalize changing levels of histones protein to levels of other proteins that do not change their levels of expression under various cellular conditions.

4. These assays can be applied to both unmodified fragment peptides and to modified fragment peptides of the target proteins, where the modifications include, but are not limited to phosphorylation and/or glycosylation, acetylation, methylation (mono, di, tri), citrullination, ubiquitinylation and where the relative levels of modified peptides are determined in the same manner as determining relative amounts of unmodified peptides.

Absolute quantification of a given peptide may be achieved by:

1. Comparing the SRM/MRM signature peak area for a given fragment peptide from the target proteins in an individual biological sample to the SRM/MRM signature peak area of an internal fragment peptide standard spiked into the protein lysate from the biological sample. The internal standard may be a labeled synthetic version of the fragment peptide from the target protein that is being interrogated or the labeled recombinant protein. This standard is spiked into a sample in known amounts before (mandatory for the recombinant protein) or after digestion, and the SRM/MRM signature peak area can be determined for both the internal fragment peptide standard and the native fragment peptide in the biological sample separately, followed by comparison of both peak areas. This can be applied to unmodified fragment peptides and modified fragment peptides, where the modifications include but are not limited to phosphorylation and/or glycosylation, acetylation, methylation (e.g. mono-, di-, or tri-methylation), citrullination, ubiquitinylation, and where the absolute levels of modified peptides can be determined in the same manner as determining absolute levels of unmodified peptides.

2. Peptides can also be quantified using external calibration curves. The normal curve approach uses a constant amount of a heavy peptide as an internal standard and a varying amount of light synthetic peptide spiked into the sample. A representative matrix similar to that of the test samples needs to be used to construct standard curves to account for a matrix effect. Besides, reverse curve method circumvents the issue of endogenous analyte in the matrix, where a constant amount of light peptide is spiked on top of the endogenous analyte to create an internal standard and varying amounts of heavy peptide are spiked to create a set of concentration standards. Test samples to be compared with either the normal or reverse curves are spiked with the same amount of standard peptide as the internal standard spiked into the matrix used to create the calibration curve.

The invention further relates to kits, the use of the kits and methods wherein such kits are used. The invention relates to kits for carrying out the herein above and below provided methods. The herein provided definitions, e.g. provided in relation to the methods, also apply to the kits of the invention. In particular, the invention relates to kits for therapy monitoring, comprising the prognosis, risk assessment or risk stratification of a subsequent adverse event in the health of a patient, wherein said kit comprises detection reagents for determining the level proADM or fragment(s) thereof, and optionally additionally for determining the level of PCT, lactate and/or C-reactive protein or fragment(s) thereof, in a sample from a subject, and—detection reagents for determining said level of ADM in said sample of said subject, and reference data, such as a reference level, corresponding to high and/or low severity levels of ADM, wherein the low severity level is below 4 nmol/l, preferably below 3 nmol/l, more preferably below 2.7 nmol/l, and the high severity level is above 6.5 nmol/l, preferably above 6.95 nmol/l, more preferably above 10.9 nmol/l, and optionally PCT, lactate and/or C-reactive protein levels, wherein said reference data is preferably stored on a computer readable medium and/or employed in the form of computer executable code configured for comparing the determined levels of proADM or fragment(s) thereof, and optionally additionally the determined levels of PCT, lactate and/or C-reactive protein or fragment(s) thereof, to said reference data.

As used herein, "reference data" comprise reference level (s) of ADM and optionally PCT, lactate, C-reactive protein and/or other suitable markers disclosed herein, such as for example markers of rhabdomyolysis. The levels of ADM and optionally other markers such as PCT, lactate and/or C-reactive protein in the sample of the subject can be compared to the reference levels comprised in the reference data of the kit. The reference levels are herein described above and are exemplified also in the appended examples. The reference data can also include a reference sample to which the level of ADM and optionally PCT, lactate and/or C-reactive protein is compared. The reference data can also include an instruction manual how to use the kits of the invention.

The kit may additionally comprise items useful for obtaining a sample, such as a blood sample, for example the kit may comprise a container, wherein said container comprises a device for attachment of said container to a cannula or syringe, is a syringe suitable for blood isolation, exhibits an internal pressure less than atmospheric pressure, such as is suitable for drawing a pre-determined volume of sample into said container, and/or comprises additionally detergents, chaotropic salts, ribonuclease inhibitors, chelating agents, such as guanidinium isothiocyanate, guanidinium hydrochloride, sodium dodecylsulfate, polyoxyethylene sorbitan monolaurate, RNAse inhibitor proteins, and mixtures thereof, and/or A filter system containing nitro-cellulose, silica matrix, ferromagnetic spheres, a cup retrieve spill over, trehalose, fructose, lactose, mannose, poly-ethylenglycol, glycerol, EDTA, TRIS, limonene, xylene, benzoyl, phenol, mineral oil, anilin, pyrol, citrate, and mixtures thereof.

As used herein, the "detection reagent" or the like are reagents that are suitable to determine the herein described marker(s), e.g. of ADM, PCT, lactate and/or C-reactive protein. Such exemplary detection reagents are, for example, ligands, e.g. antibodies or fragments thereof, which specifically bind to the peptide or epitopes of the herein described marker(s). Such ligands might be used in immunoassays as described above. Further reagents that are employed in the immunoassays to determine the level of the marker(s) may also be comprised in the kit and are herein considered as detection reagents. Detection reagents can also relate to reagents that are employed to detect the markers or fragments thereof by MS based methods. Such detection reagent can thus also be reagents, e.g. enzymes, chemicals, buffers, etc, that are used to prepare the sample for the MS analysis. A mass spectrometer can also be considered as a detection reagent. Detection reagents according to the invention can also be calibration solution(s), e.g. which can be employed to determine and compare the level of the marker(s).

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having an infection and "disease" populations, e.g. subjects having an infection. For any particular marker (like ADM), a distribution of marker levels for subjects with and without a disease/condition will likely overlap. Under such conditions, a test does not absolutely distinguish normal from disease with 100% accuracy, and the area of overlap might indicate where the test cannot distinguish normal from disease. A threshold is selected, below which the test is considered to be abnormal and above which the test is considered to be normal or below or above which the test indicates a specific condition, e.g. infection. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art; see, e.g., Hanley et al. 1982. Radiology 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/− 5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

Accordingly, the invention comprises the administration of an antibiotic suitable for treatment on the basis of the information obtained by the method described herein.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

Thus, the terms "comprising"/"including"/"having" mean that any further component (or likewise features, integers, steps and the like) can/may be present. The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

The present invention is further described by reference to the following non-limiting examples.

EXAMPLES

Methods of the Examples:
Study Design and Patients:

This is a secondary analysis of the Improvement of prognostic performance in severely injured patients by integrated clinico-transcriptomics: a translational approach study [14], which was conducted between December 2009 and March 2012 in patients admitted to the Division of Trauma Surgery (a level 1 trauma centre) at the University Hospital of Zurich. Patient inclusion criteria included those aged ≥18 years, an Injury Severity (ISS) score of ≥17 points, and a time from injury to admission of <6 hours. Further details of the original study design have been described previously [14].

Blood Sample Measurements and Clinical Data Collection:

Blood samples from trauma patients were collected within the first 6 hours after trauma (baseline), as well as on days 1, 2, 3, 5, 7, 10, 14 and 24 thereafter. Clinical outcomes, including nosocomial infections, sepsis development and non-infection related complications, were recorded within the first 28 days after initial trauma. Systemic inflammation was defined according to the criteria of the American College of Chest Physicians/Society of Critical care Medicine Consensus Conference [15, 16]. The Systemic Inflammation score (SI score) [17] was used to assess the severity of trauma-induced systemic inflammation. Subsequent sepsis development in trauma patients was defined as an increase of ≥2 SI points between two consecutive time points, in the presence of an infectious focus or a positive blood culture. Sequential organ failure assessment (SOFA) scores were calculated at all time points.

Procalcitonin (PCT) and Mid-regional proadrenomedullin (MR-proADM) concentrations were measured retrospectively (KRYPTOR® assay, Thermo Fisher Scientific, Germany) with a limit of detection of 0.05 nmol/L and 0.02 ng/ml. CRP and lactate concentrations were measured locally.

Statistical Analysis:

Differences in patient demographics and clinical characteristics were assessed using the $\chi^2$ test for categorical variables, and Student's t-test or Mann-Whitney U test for continuous variables, depending on distribution normality. Normally and non-normally distributed variables were expressed as mean (standard deviation) and median [first quartile-third quartile], respectively. The association between each clinical score (SOFA and ISS) and biomarker was assessed at baseline and day 1. The total number of surgeries and their duration was noted in each case, along with the requirement for antibiotic administration at baseline and over the first 7 days of hospitalisation. The presence of nosocomial infections were identified and classified as either surgical or non-surgical related.

Models of biomarker and clinical score kinetics between baseline and day 1 were subsequently created in order to assess the likelihood of sepsis development or non-infection related complications over the first 28 days after trauma. Pre-established cut-offs for MR-proADM (<1.54 nmol/L) [SIDED], PCT (<0.5 ng/mL), lactate (<2.0 mmol/L) [8] and SOFA (<5 points) were used at both time points. Resulting odds ratios (OR) assessed the likelihood of adverse events between the different patient subgroups.

Example 1: Patient Characteristics

Patient characteristics are summarized in Table 1.

A total of 77 patients had samples available for biomarker measurement which could be retrospectively analysed, of which 74.0% (N=57) were male, the average age was 41.4 (17.3) years and the 28 day mortality rate was 6.5% (N=5). The mean Glasgow Coma Scale (GCS) score on admission was 12.3 (4.0) points with 16 (20.8%) patients having a GCS of <10 points. All patients were admitted onto the ICU, with a median length of ICU and overall hospitalisation of 12 [4-21] and 25 [16-38] days, respectively.

Patients had an average of 4.3 (2.7) operations over the first 28 days following initial trauma, with emergency surgery performed in 71 (92.2%) patients at baseline. A further 20 operations were performed on day 1, of which 16 (80.0%) were repeat surgeries and 4 (20.0%) were on patients not operated on at baseline. Only 2 (2.6%) patients did not require any form of surgical intervention throughout hospitalisation. The average length of surgery was 116.2 (92.0) minutes.

Example 2: Sepsis and Non-infection Related Complication Development

A total of 44 (57.9%) patients developed a non-infection related complication over 28 days, with Rhabdomyolysis development the most common complication (N=15; 34.1%). Conversely, 48 (64.9%) patients developed a nosocomial infection, with surgical and non-surgical infections accounting for 19 (38.0%) and 27 (54.0%) cases, respectively. Non-surgical ventilator associated pneumonia was found in 12 (44.4%) patients. Of the 48 patients that developed nosocomial infections, 12 (24.0%) developed sepsis, with a mean time to diagnosis of 9.5 (4.7) days, of which 10 (83.3%) progressed onto septic shock. Patient characteristics with regards to sepsis development can be found in Table 1.

Antibiotics were administered to 44 (57.1%) patients at baseline, 45 (58.4%) at either baseline or day 1, and 55 (71.4%) during the first 7 days of hospitalisation. Of the 45 patients who were administered antibiotics at either baseline or day 1, antibiotics were initiated in 11 (24.4%) patients who subsequently did not develop any infection, in contrast to 32 (71.1%) patients who developed nosocomial infections. A total of 11 (91.7%) patients who developed sepsis were administered antibiotics within the first seven days of treatment.

Example 3: Correlation of Biomarker and Clinical Scores at Baseline

There was no significant correlation between any of the biomarkers and the SOFA score on admission, whereas a low but significant association could be found between lactate, SOFA and MR-proADM and the ISS score. SOFA and lactate had the greatest correlation with ICU length of stay at baseline, whereas there was no significant correlation with either PCT or CRP.

Interestingly, lactate also had the highest correlation with the total length of patient hospitalisation.

Example 4: Prediction of Sepsis Development at Baseline and Day 1

MR-proADM and SOFA were the only two parameters that were significantly associated with predicting sepsis development both at baseline (AUROC [95% CI]: 0.71 [0.56-0.86] and 0.73 [0.56-0.90]) and at day 1 (AUROC [95% CI]: 0.85 [0.76-0.94] and 0.84 [0.70-0.98]), although all parameters showed improved performance one day following trauma (Table 2).

Similarities could also be found in the development of non-infection related complications, with MR-proADM and lactate the only two parameters to have a significant association at both baseline and day 1. Conversely, CRP showed no significant association at either time point (Table 3).

Example 5: Kinetical Models Predicting Sepsis and Trauma Related Complications

Biomarkers and clinical scores were subsequently identified according to their predictive performance at baseline and day 1 in order to either rule-in/rule-out sepsis development within 28 days, or identify a patient population at a high risk of developing non-infection related complications within the same time period.

Example 6: Sepsis Development Over 28 Days

Lactate and MR-proADM were subsequently investigated in order to predict trauma related complication development over 28 days. In contrast to patients who developed sepsis, lactate levels <2 mmol/L between baseline and day 1 could identify a lower number of trauma related complications (N=7; 28.0%) in comparison to continuously low levels of MR-proADM (N=16; 40.0%). Conversely, increasing (14 patients, 87.5% complication rate) or continuously elevated (8 patients, 88.9% complication rate) MR-proADM concentrations could accurately identify subgroups at risk of potential complication development.

Discussion of Examples

This retrospective analysis compared the performance of established and novel biomarkers and clinical scores in the early rule-in or rule-out of sepsis after severe polytrauma. The maintenance of continuously low MR-proADM or high SOFA levels to either rule-out or rule-in sepsis development, respectively, may aid in the development of specific treatment strategies based on secondary complications due to infection.

Tables

TABLE 1

Patient characteristics at baseline based on subsequent sepsis development status.

| Patient characteristic | Total population (N = 77) | Sepsis population (N = 12) | Non-Sepsis population (N = 65) | p-value |
|---|---|---|---|---|
| Demographics | | | | |
| Age (years) | 41.4 (17.3) | 41.5 (17.3) | 40.6 (17.7) | |
| Male sex (n, %) Glasgow Coma Scale score | 10.4 (5.4) | 6.7 (5.4) | 11.1 (5.2) | |
| Injury Severity Score | 33.4 (11.9) | 41.4 (10.4) | 31.9 (11.7) | |
| Emergency operations | 4.3 (2.7) | 7.3 (2.8) | 3.7 (2.4) | |
| Laboratory values | | | | |
| Temperature | 35.1 (1.3) | 37.8 (1.0) | 35.2 (1.4) | |
| Leucocytes | 152 (6.5) | 16.9 (9.5) | 14.9 (5.8) | |
| Hamatocrit | 30.6 (7.5) | 25.9 (9.2) | 31.4 (6.9) | |
| Thrombocytes | 208.0 (66.0) | 176.4 (52.0) | 213.8 (67.0) | |
| aPTT | 34.7 (19.5) | 30.6 (8.3) | 30.6 (8.3) | |

TABLE 1-continued

Patient characteristics at baseline based on subsequent sepsis development status.

| Patient characteristic | Total population (N = 77) | Sepsis population (N = 12) | Non-Sepsis population (N = 65) | p-value |
|---|---|---|---|---|
| Allogenic blood transfusion | | | | |
| TASH score (points) | 8.8 (5.6) | 15.3 (6.2) | 7.8 (4.9) | |
| TASH (%) | 14.9 (19.8) | 37.8 (32.8) | 11.4 (14.4) | |
| Total pRBC transfusion | 10.2 (14.7) | 28.8 (25.3) | 6.8 (8.4) | |
| Outcomes | | | | |
| RISC (% survival) | 83.3 (24.1) | 72.7 (27.9) | 85.3 (23.1) | |
| 28 day survival (n, %) | 72 (94.0%) | | | |
| ICU length of stay (days) | 14.8 (14.2) | 34.2 (19.3) | 11.1 (9.3) | <0.001 |
| Hospital length of stay (days) | 29.1 (19.5) | 54.7 (29.5) | 24.4 (12.6) | <0.001 |
| Biomarker concentrations | | | | |
| MR-proADM (nmol/L) | 0.78 | 0.71 | 0.71 | 0.021 |
| PCT | 0.06 | 0.05 | 0.05 | 0.267 |
| CRP | 0.8 | 0.9 | 0.75 | 0.988 |
| Lactate | 2.1 | 2.0 | 2.6 | 0.227 |
| SOFA | 4.7 (3.2) | 6.9 (3.2) | 4.3 (3.1) | 0.018 |
| SIRS (points) | 3.5 (1.4) | 4.7 (1.2) | 3.3 (1.3) | |

TABLE 2

Biomarker and clinical score performance at baseline and day 1 for the prediction of sepsis development over 28 days.

| | | Cut-off | AUROC | Sensitivity | Specificity | PPV | NPV |
|---|---|---|---|---|---|---|---|
| Baseline | MR-proADM | 0.97 | 0.71 [0.56-0.86 | 0.75 [0.47-0.91 | 0.63 [0.51-0.74 | 0.29 [0.16-0.47 | 0.93 [0.81-0.97 |
| | PCT | 0.23 | 0.60 [0.43-0.78 | 0.42 [0.19-0.68 | 0.83 [0.72-0.91 | 0.33 [0.15-0.58 | 0.88 [0.77-0.94 |
| | Lactate | 4.8 | 0.61 [0.40-0.82 | 0.42 [0.19-0.68 | 0.91 [0.81-0.96 | 0.45 [0.21-0.72 | 0.89 [0.80-0.95 |
| | CRP | 0.6 | 0.50 [0.32-0.68 | 0.75 [0.47-0.91 | 0.42 [0.30-0.54 | 0.19 [0.10-0.33 | 0.90 [0.74-0.97 |
| | SOFA | 7 | 0.73 [0.56-0.90 | 0.75 [0.47-0.91 | 0.73 [0.62-0.83 | 0.35 [0.19-0.54 | 0.94 [0.84-0.98 |
| Day 1 | MR-proADM | 1.35 | 0.85 [0.76-0.94 | 1.00 [0.76-1.00 | 0.66 [0.53-0.76 | 0.36 [0.22-0.53 | 1.00 [0.91-1.00 |
| | PCT | 2.10 | 0.85 [0.73-0.97 | 0.83 [0.55-0.95 | 0.77 [0.65-0.86 | 0.42 [0.24-0.61 | 0.96 [0.86-0.99 |
| | Lactate | 2.7 | 0.81 [0.65-0.97 | 0.75 [0.47-0.91 | 0.86 [0.75-0.92 | 0.50 [0.29-0.71 | 0.95 [0.86-0.98 |
| | CRP | 6.3 | 0.72 [0.56-0.88 | 1.00 [0.76-1.00 | 0.03 [0.01-0.11 | 0.17 [0.10-0.27 | 1.00 [0.34-1.00 |
| | SOFA | 10 | 0.84 [0.70-0.98 | 0.75 [0.47-0.91 | 0.83 [0.72-0.90 | 0.45 [0.26-0.66 | 0.95 [0.86-0.98 |

TABLE 3

Biomarker and clinical score performance at baseline
and day 1 for the prediction of non-infection related complications
over 28 days.

| | | Cut-off | AUROC | Sensitivity | Specificity | PPV | NPV |
|---|---|---|---|---|---|---|---|
| Baseline | MR-proADM | 0.82 | 0.68 [0.56-0.81] | 0.67 [0.52-0.79] | 0.66 [0.47-0.80] | 0.74 [0.58-0.85] | 0.58 [0.41-0.73] |
| | PCT | 0.05 | 0.60 [0.46-0.74] | 0.75 [0.61-0.85] | 0.62 [0.45-0.77] | 0.73 [0.59-0.84] | 0.65 [0.47-0.79] |
| | Lactate | 1.8 | 0.73 [0.61-0.85] | 0.98 [0.88-1.00] | 0.03 [0.01-0.16] | 0.58 [0.47-0.69] | 0.50 [0.09-0.91] |
| | CRP | 0.3 | 0.59 [0.46-0.73] | 0.28 [0.17-0.43] | 0.88 [0.72-0.95] | 0.75 [0.51-0.90] | 0.47 [0.35-0.60] |
| | SOFA | 8 | 0.60 [0.47-0.72] | 0.67 [0.52-0.79] | 0.66 [0.47-0.80] | 0.74 [0.58-0.85] | 0.58 [0.41-0.73] |
| Day 1 | MR-proADM | 0.97 | 0.76 [0.64-0.87] | 0.79 [0.64-0.88] | 0.67 [0.49-0.81] | 0.77 [0.62-0.87] | 0.69 [0.51-0.83] |
| | PCT | 0.97 | 0.75 [0.64-0.87] | 0.64 [0.49-0.77] | 0.80 [0.63-0.90] | 0.82 [0.66-0.91] | 0.62 [0.46-0.75] |
| | Lactate | 2.2 | 0.68 [0.55-0.80] | 0.51 [0.37-0.65] | 0.84 [0.67-0.93] | 0.81 [0.63-0.92] | 0.55 [0.41-0.69] |
| | CRP | 141 | 0.54 [0.40-0.67] | 0.17 [0.09-0.31] | 0.97 [0.84-0.99] | 0.88 [0.53-0.98] | 0.48 [0.36-0.60] |
| | SOFA | 9 | 0.67 [0.55-0.79] | 0.48 [0.34-0.62] | 0.81 [0.65-0.91] | 0.78 [0.59-0.89] | 0.53 [0.39-0.66] |

TABLE 4

Likelihood of sepsis development according
to biomarker and clinical score values.

| | Biomarker Kinetics | | Patients | Sepsis development | Trauma complications |
|---|---|---|---|---|---|
| | Baseline | Day 1 | (N) | N (%) | N (%) |
| ADM level | Low | Low | 40 | 0 (0.0%) | 16 (40.0%) |
| | Low | High | 17 | 8 (47.1%) | 14 (87.5%) |
| | High | Low | 3 | 1 (33.3%) | 2 (66.7%) |
| | High | High | 9 | 3 (33.3%) | 8 (88.9%) |
| PCT level | Low | Low | 25 | 1 (4.0%) | 10 (40.0%) |
| | Low | High | 38 | 10 (26.3%) | 27 (70.3%) |
| | High | Low | 0 | NA | NA |
| | High | High | 6 | 1 (16.7%) | 4 (66.7%) |
| Lactate level | Low | Low | 26 | 2 (7.7%) | 7 (28.0%) |
| | Low | High | 6 | 2 (33.3%) | 5 (83.3%) |
| | High | Low | 16 | 0 (0.0%) | 11 (68.8%) |
| | High | High | 27 | 8 (29.6%) | 20 (74.1%) |
| SOFA level | Low | Low | 25 | 1 (4.0%) | 11 (44.0%) |
| | Low | High | 14 | 2 (14.3%) | 9 (64.3%) |
| | High | Low | 4 | 0 (0.0%) | 2 (50.0%) |
| | High | High | 33 | 9 (27.3%) | 21 (65.6%) |

REFERENCES

1. Mock C N, Jurkovich G J, nii-Amon-Kotei D, Arreola-Risa C, Maier R V. Trauma mortality patterns in three nations at different economic levels: implications for global trauma system development. J Trauma. 1998 May; 44(5):804-12; discussion 12-4.
2. MacKenzie E J. Epidemiology of injuries: current trends and future challenges. Epidemiol Rev. 2000; 22(1):112-9.
3. Wafaisade A, Lefering R, Bouillon B, Sakka S G, Thamm O C, Paffrath T, et al. Epidemiology and risk factors of sepsis after multiple trauma: an analysis of 29,829 patients from the Trauma Registry of the German Society for Trauma Surgery. Crit Care Med. 2011 April; 39(4): 621-8.
4. Hirsiger S, Simmen H P, Werner C M, Wanner G A, Rittirsch D. Danger signals activating the immune response after trauma. Mediators Inflamm. 2012; 2012: 315941.
5. Gentile L F, Cuenca A G, Efron P A, Ang D, Bihorac A, McKinley B A, et al. Persistent inflammation and immunosuppression: a common syndrome and new horizon for surgical intensive care. J Trauma Acute Care Surg. 2012 June; 72(6):1491-501.
6. Wanner G A, Keel M, Steckholzer U, Beier W, Stocker R, Ertel W. Relationship between procalcitonin plasma levels and severity of injury, sepsis, organ failure, and mortality in injured patients. Crit Care Med. 2000 April; 28(4):950-7.
7. Gebhard F, Huber-Lang M. Polytrauma-pathophysiology and management principles. Langenbecks Arch Surg. 2008 November; 393(6):825-31.
8. Singer M, Deutschman C S, Seymour C W, Shankar-Hari M, Annane D, Bauer M, et al. The Third International Consensus Definitions for Sepsis and Septic Shock (Sepsis-3). JAMA. 2016 Feb. 23; 315(8):801-10.
9. Gille J, Ostermann H, Dragu A, Sablotzki A. MR-proADM: A New Biomarker for Early Diagnosis of Sepsis in Burned Patients. J Burn Care Res. 2017 September/October; 38(5):290-8.
10. Bustamante A, Garcia-Berrocoso T, Penalba A, Giralt D, Simats A, Muchada M, et al. Sepsis biomarkers reprofiling to predict stroke-associated infections. J Neuroimmunol. 2017 Nov. 15; 312:19-23.
11. Andaluz-Ojeda D, Nguyen H B, Meunier-Beillard N, Cicuendez R, Quenot J P, Calvo D, et al. Superior accuracy of mid-regional proadrenomedullin for mortality prediction in sepsis with varying levels of illness severity. Ann Intensive Care. 2017 December; 7(1):15.
12. Charles P E, Peju E, Dantec A, Bruyere R, Meunier-Beillard N, Dargent A, et al. Mr-Proadm Elevation Upon Icu Admission Predicts the Outcome of Septic Patients and is Correlated with Upcoming Fluid Overload. Shock. 2017 October; 48(4):418-26.
13. Bernal-Morell E, Garcia-Villalba E, Vera M D C, Medina B, Martinez M, Callejo V, et al. Usefulness of midregional pro-adrenomedullin as a marker of organ damage and predictor of mortality in patients with sepsis. J Infect. 2017 Dec. 12.

14. Rittirsch D, Schoenborn V, Lindig S, Wanner E, Sprengel K, Gunkel S, et al. Improvement of prognostic performance in severely injured patients by integrated clinico-transcriptomics: a translational approach. Crit Care. 2015 Nov. 26; 19:414.

15. Bone R C, Balk R A, Cerra F B, Dellinger R P, Fein A M, Knaus W A, et al. Definitions for sepsis and organ failure and guidelines for the use of innovative therapies in sepsis. The ACCP/SCCM Consensus Conference Committee. American College of Chest Physicians/Society of Critical Care Medicine. Chest. 1992 June; 101(6):1644-55.

16. Levy M M, Fink M P, Marshall J C, Abraham E, Angus D, Cook D, et al. 2001 SCCM/ESICM/ACCP/ATS/SIS International Sepsis Definitions Conference. Crit Care Med. 2003 April; 31(4):1250-6.

17. Rangel-Frausto M S, Pittet D, Costigan M, Hwang T, Davis C S, Wenzel R P. The natural history of the systemic inflammatory response syndrome (SIRS). A prospective study. JAMA. 1995 Jan. 11; 273(2):117-23.

The invention claimed is:

1. A method of reducing the risk of a subsequent poly-trauma-related complication in a polytrauma patient, comprising:

a) providing a sample from the patient after the poly-trauma;

b) measuring a level of mid-regional proadrenomedullin (MR-proADM) in the patient sample, and comparing said level to a reference level of 2.25 nmol/L, wherein the level of MR-proADM in the patient sample is above said reference level; and c) administering treatment to the patient in an intensive care unit (ICU) to reduce the risk of the subsequent polytrauma-related complication;

wherein the treatment comprises an antibiotic treatment, one or more of anti-inflammatory agents, extracorporeal blood treatment to remove harmful substances via apheresis, adsorption, dialysis, mechanical ventilation, organ replacement therapy, hemofiltration, intravenous fluids, sodium bicarbonate, mannitol, calcium, insulin, or salbutamol;

wherein the subsequent polytrauma-related complication is a non-infection related complication, or an infection related complication; and wherein the patient has multiple traumata corresponding to an Injury Severity Score of at least 17 points.

2. The method of claim 1, wherein the subsequent poly-trauma-related complication comprises rhabdomyolysis and the treatment comprises one or more of dialysis, hemofil-tration, intravenous fluids, sodium bicarbonate, mannitol, calcium, insulin, or salbutamol.

3. The method of claim 1, wherein the subsequent trauma-related complication is an infection and the treatment com-prises an antibiotic treatment.

4. The method of claim 3, wherein the antibiotic treatment comprises an antibacterial compound for treatment of Gram-positive bacteria, an antibacterial compound for treatment of Gram-negative bacteria, an antifungal compound, an anti-viral compound, a bacteriophage, an iron antagonist, a synthesized antimicrobial peptide, and any combination thereof.

5. The method of claim 4, wherein the antibiotic treatment is administered intravenously, orally, and/or topically.

6. The method of claim 3, wherein the infection comprises nosocomial infection, sepsis, septic shock, and/or rhab-domyolysis.

7. The method of claim 1, wherein the patient sample is chosen from a blood sample and a urine sample.

8. The method of claim 1, wherein the patient sample was obtained within 24 hours of the polytrauma.

9. The method of claim 1, wherein the patient sample was obtained from 24 hours to 48 hours after the polytrauma.

10. The method of claim 3, wherein the treatment is administered when the level of MR-proADM in a patient sample obtained within 24 hours of the polytrauma is equal to or greater than a reference level of 0.97 nmol/L±20% ranging from 0.78 nmol/L to 1.16 nmol/L, or wherein the treatment is administered when the level of MR-proADM in a patient sample obtained from 24 and 48 hours after the polytrauma is equal to or greater than a reference level of 1.35 nmol/L±20% ranging from 1.08 nmol/L to 1.62 nmol/L.

11. The method of claim 8, wherein the levels of MR-proADM in a patient sample that is obtained from 24 hours to 48 hours after the polytrauma are higher than levels of MR-proADM in the sample obtained within 24 hours after the polytrauma.

12. The method of claim 3, wherein the infection is an infection that has yet to occur.

13. The method of claim 1, wherein the subsequent polytrauma-related complication occurs within 28 days of the polytrauma.

14. The method of claim 1, additionally comprising determining a Sequential Organ Failure Assessment (SOFA) score.

15. The method of claim 1, additionally comprising determining a level of at least one additional biomarker which is Procalcitonin (PCT).

16. The method of claim 1, wherein the patient sample is obtained within 6 hours of the polytrauma.

17. A method for measuring a level of MR-proADM in a patient sample from a polytrauma patient, comprising: pro-viding a sample from the patient after the polytrauma, measuring a level of MR-proADM in the patient sample, and comparing said level to a reference level of 2.25 nmol/L, and wherein said measured level of MR-proADM in the patient sample is above the reference level, and wherein the patient has multiple traumata corresponding to an Injury Severity Score of at least 17 points, and is in an intensive care unit (ICU).

18. The method of claim 1, wherein the non-infection related complications or the infection related complications are associated with organ failure.

19. A method of reducing the risk of a subsequent polytrauma-related complication in a polytrauma patient, comprising:

a) providing a sample from the patient after the poly-trauma;

b) measuring a level of mid-regional proadrenomedullin (MR-proADM) in the patient sample, and comparing said level to a reference level of 2.25 nmol/L±20%, wherein the level of MR-proADM in the patient sample is above said reference level; and c) administering treatment to the patient in an intensive care unit (ICU) to reduce the risk of the subsequent polytrauma-related complication, wherein the treat-ment comprises an antibiotic treatment, one or more anti-inflammatory treatments, extracorporeal blood treatment to remove harmful substances via apheresis, adsorption, dialysis, mechanical ventilation, organ replacement therapy, hemofiltration, sodium bicarbon-ate, mannitol, calcium, insulin, or salbutamol;

wherein the subsequent polytrauma-related complication is a non-infection related complication, or an infection related complication; and wherein the patient has multiple traumata corresponding to an Injury Severity Score of at least 17 points.

20. A kit for carrying out the method of claim 1, com-prising:

a) detection reagents for determining the level MR-proADM, and optionally additionally for determining the level of at least one additional biomarker in a sample from a subject; and b) reference data, such as one or more reference levels, corresponding to i) a reference level of MR-proADM in a sample obtained within 24 hours after the trauma equal to or greater than 0.82 nmol/L±20% ranging from 0.66 nmol/L to 0.98 nmol/L for the treatment of a non-infectious trauma-related complication;

ii) a reference level of MR-proADM in a sample obtained from 24 and 48 hours after the trauma equal to or greater than 0.97 nmol±20% ranging from 0.78 nmol/L to 1.16 nmol/L for the treatment of a non-infectious trauma-related complication;

iii) a reference level of MR-proADM in a sample obtained within 24 hours after the trauma equal to or greater than 0.97 nmol/L±20% ranging from 0.78 nmol/L to 1.16 nmol/L for the treatment of an infection;

iv) a reference level of MR-proADM in a sample obtained from 24 hours to 48 hours after the trauma equal to or greater than 1.35 nmol±20% for the treatment of an infection; and/or v) high and/or low severity levels of MR-proADM, wherein the low severity level is less than 1.54 nmol/L±20% ranging from 1.23 nmol/L to 1.85 nmol/L and the high severity level is equal to or greater than 1.54 nmol/L±20% ranging from 1.23 nmol/L to 1.85 nmol/L;

wherein said reference data is stored on a computer readable medium and/or employed in the form of a computer executable code configured for comparing the determined levels of MR-proADM, and optionally additionally the determined levels of at least one additional biomarker, to said reference data.

\* \* \* \* \*

SEQUENCE LISTING

```
<160> NUMBER OF SEQ ID NOS: 2

<210> SEQ ID NO 1
<211> LENGTH: 185
<212> TYPE: PRT
<213> ORGANISM: Homo sapiens

<400> SEQUENCE: 1

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 2
<211> LENGTH: 48
<212> TYPE: PRT
<213> ORGANISM: Homo sapiens

<400> SEQUENCE: 2

Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
        35                  40                  45
```